US009770445B2

(12) United States Patent
Kosemund et al.

(10) Patent No.: US 9,770,445 B2
(45) Date of Patent: Sep. 26, 2017

(54) SULFOXIMINE SUBSTITUTED 5-FLUORO-N-(PYRIDIN-2-YL)PYRIDIN-2-AMINE DERIVATIVES AND THEIR USE AS CDK9 KINASE INHIBITORS

(71) Applicant: BAYER PHARMA AKTIENGESELLSCHAFT, Berlin (DE)

(72) Inventors: Dirk Kosemund, Berlin (DE); Ulrich Lücking, Berlin (DE); Arne Scholz, Berlin (DE); Gerhard Siemeister, Berlin (DE); Philip Alexander Lienau, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 14/903,364

(22) PCT Filed: Jul. 3, 2014

(86) PCT No.: PCT/EP2014/064184
§ 371 (c)(1),
(2) Date: Jan. 7, 2016

(87) PCT Pub. No.: WO2015/001021
PCT Pub. Date: Jan. 8, 2015

(65) Prior Publication Data
US 2016/0143893 A1 May 26, 2016

(30) Foreign Application Priority Data

Jul. 4, 2013 (EP) .................... 13175067

(51) Int. Cl.
A61K 31/444 (2006.01)
C07D 405/14 (2006.01)
C07D 401/14 (2006.01)

(52) U.S. Cl.
CPC .......... A61K 31/444 (2013.01); C07D 401/14 (2013.01); C07D 405/14 (2013.01)

(58) Field of Classification Search
CPC .............................. C07D 405/14; A61K 31/444
See application file for complete search history.

(56) References Cited

U.S. PATENT DOCUMENTS

| 2004/0209895 | A1 | 10/2004 | Luecking et al. |
| 2005/0176743 | A1 | 8/2005 | Luecking et al. |
| 2010/0184789 | A1 | 7/2010 | Wabnitz et al. |
| 2011/0028492 | A1 | 2/2011 | Barsanti et al. |
| 2011/0306602 | A1 | 12/2011 | Wabnitz et al. |

FOREIGN PATENT DOCUMENTS

| EP | 2527332 | 11/2012 |
| WO | WO-02059110 | 8/2002 |
| WO | WO-2005037800 | 4/2005 |
| WO | WO-2006064251 | 6/2006 |
| WO | WO-2008028590 | 3/2008 |
| WO | WO-2008060248 | 5/2008 |
| WO | WO-2008079918 | 7/2008 |
| WO | WO-2008079933 | 7/2008 |
| WO | WO-2008129070 | 10/2008 |
| WO | WO-2008129071 | 10/2008 |
| WO | WO-2008129080 | 10/2008 |
| WO | WO-2008132138 | 11/2008 |
| WO | WO-2009029998 | 3/2009 |
| WO | WO-2009118567 | 10/2009 |
| WO | WO-2011116951 | 9/2011 |
| WO | WO-2012117059 | 9/2012 |
| WO | WO-2013037894 | 3/2013 |
| WO | WO-2013037896 | 3/2013 |
| WO | WO-2014060376 | 4/2014 |
| WO | WO-2014076028 | 5/2014 |
| WO | WO-2014076091 | 5/2014 |
| WO | WO-2015001021 | 1/2015 |
| WO | WO-2015136028 | 9/2015 |

OTHER PUBLICATIONS

Allenmark, S. et al. (1983). "Enantioselective Liquid Chromatographic Retention of a Series of Sulfoxides and N-substituted Sulfoximines on Chiral Stationary Phases," Acta Chemica Scandinavica B 37: 325-328.
Bark-Jones, S.J. et al. (2006). "EBV EBNA 2 stimulates CDK9-dependent transcription and RNA polymerase II phosphorylation on serine 5," Oncogene 25: 1775-1785.
Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," Journal of Medicinal Chemistry 22(4): 418-424.
Bauer, V.J. et al. (Oct. 1966). "The Reactions of Carbamoyl Azides with Sulfur Nucleophiles," Journal of Organic Chemisty 31: 3440-3441.
Berge, S.M. et al. (Jan. 1977). "Pharmaceutical Salts," Journal of Pharmaceutical Sciences 66(1): 1-19.
Bolm, C. et al. (1998). "Palladium-Catalyzed Carbon-Nitrogen Bond Formation: A Novel, Catalytic Approach towards N-Arylated Sulfoximines," Tetrahedron Letters 39: 5731-5734.
Bolm, C. et al. (2000). "Palladium-Catalyzed N-Arylation of Sulfoximines with Aryl Bromides and Aryl Iodides," Journal of Organic Chemistry 65: 169-175.
Bolm, C. et al. (Feb. 2000). "Catalytic Coupling of Aryl Sulfonates with sp$^2$-Hybridized Nitrogen Nucleophiles: Palladium- and Nickel-catalyzed Synthesis of N-Aryl Sulfoximines," Synthesis 7: 911-913.

(Continued)

Primary Examiner — Barbara P Badio
Assistant Examiner — Sara E Townsley
(74) Attorney, Agent, or Firm — Morrison & Foerster LLP

(57) ABSTRACT

The present invention relates to 5-fluoro-N-(pyridin-2-yl)pyridin-2-amine derivatives containing a sulfoximine group of general formula (I) as described and defined herein, and methods for their preparation, their use for the treatment and/or prophylaxis of disorders, in particular of hyperproliferative disorders and/or virally induced infectious diseases and/or of cardiovascular diseases. The invention further relates to intermediate compounds useful in the preparation of said compounds of general formula (I).

12 Claims, No Drawings

(56) References Cited

OTHER PUBLICATIONS

Bolm, C. et al. (2001). "Synthesis of Pseudopeptides with Sulfoximines as Chiral Backbone Modifying Elements," *Chem. Eur. J.* 7(5): 1118-1128.
Bolm, C. et al. (2002). "A Mild Synthetic Procedure for the Preparation of N-Alkylated Sulfoximines," *Synthesis* 7: 879-887.
Cho, G.Y., et al. (2005). "Synthesis and Palladium-Catalyzed Coupling Reaction of Enantiopure p-Bromophenyl Methyl Sulfoximine," *J. Org. Chem.* 70(6): 2346-2349.
Cho, S. et al. (May 1, 2010). "CYCLINg through transcription Posttranslational modification of P-TEFb regulate transcription elongation," *Cell Cycle* 9(9): 1697-1705.
Copeland, R. A. et al. (2006). "Drug-target residence time and its implications for lead optimization," *Nature Reviews Drug Discovery* 5: 730-739.
Craig, D. et al. (1995). "Asymmetric Intramolecular Diels-Alder Reactions of Sulfoximine-activated Trienes," *Tetrahedron* 51(21): 6071-6098.
Cram, D.J. (Dec. 16, 1970). "Stereochemistry of Sulfur Compounds. I. Stereochemical Reactions Cycles Involving an Open Chain Sulfoxide, Sulfimide, and Sulfoximide," *Journal of the American Chemical Society* 92(25): 7369-7384.
De Meijere, A. et al. (2004). "Metal-Catalyzed Cross-Coupling Reactions," *Wiley-VCH Verlag GmbH & Co. KGaA, Weinheim*, pp. 83-91.
Dey, A. et al. (Aug. 1, 2007). "HEXIM1 and the Control of Transcription Elongation from Cancer and Inflammation to AIDS and Cardiac Hypertrophy," *Cell Cycle* 6(15): 1856-1863.
Füger, B. et al. (2009). "Ring-Closing Enyne Metathesis (RCEYM) for the Synthesis of Cyclic Sulfoximines," *Synlett* 10: 1601-1604.
Hackenberger, C.P.R., et al. (2004). "Synthetic and Spectroscopic Investigation of N-Acylated Sulfoximines," *Chem. Eur. J.* 10: 2942-2952.
He, N. et al. (Mar. 14, 2008). "A La-Related Protein Modulates 7SK snRNP Integrity to Suppress P-TEFb-Dependent Transcriptional Elongation and Tumorigenesis," *Molecular Cell* 29: 588-599.
International Search Report mailed Sep. 5, 2014 for PCT Application No. PCT/EP2014/064184, filed on Jul. 3, 2014, 3 pages.
Johnson, C.R. (Nov. 4, 1970). "Preparation and Synthetic Applications of (Dimethylamino)phenyloxosulfonium Methylide," *Journal of the American Chemical Society* 92(22): 6594-6598.
Johnson, C.R. (1978). "Preparation of α-Halo Sulfoximines," *Journal of Organic Chemistry* 43(21): 4136-4140.
Johnson, C.R. et al. (1993). "Alkylation of Sulfoximines and Related Compounds at the Imino Nitrogen under Phase-Transfer Conditions," *Journal of Organic Chemistry* 58(7): 1922-1923.
Jones, M.R. et al. (Apr. 3, 1974). "Stereochemisty of Sulfur Compounds. VII. Course of Substitution at Sulfur Attached to Four Different Ligands," *Journal of the American Chemical Society* 96(7): 2183-2190.
Mancheño, O.G. et al. (2007). "Synthesis of N-(1 H)-Tetrazole Sulfoximines," *Organic Letters* 9(15) 2951-2954.
Okamura, H. et al. (2004). "Rhodium-Catalyzed Imination of Sulfoxides and Sulfides: Efficient Preparation of N-Unsubstituted Sulfoximines and Sulfilimines," *Organic Letters* 6(8): 1305-1307.
Polla, M.O. et al. (2004). "Design and synthesis of potent, orally active, inhibitors of carboxypeptidase U (TAFla)," *Bioorganic & Medicinal Chemistry Letters* 12: 1151-1175.
Sammond, D.M. et al. (2005). "Discovery of a novel and potent series of dianilinopyrimidineurea and urea isostere inhibitors of VEGFR2 tyrosine kinase," *Bioorganic & Medicinal Chemistry Letters* 15: 3519-3523.
Sauer, D.T. et al. (1972). "Bis(perfluoroalkyl)sulfur Oxyimines and Silver Bis(trifluoromethyl)sulfur Oxyimine," *Inorganic Chemistry* 11(2): 238-242.
Stoss, P. et al. (1978). "Transannulare Acylwanderungen in cyclischen Sulfoximiden," *Chem. Ber.* 111: 1453-1463.
Wang, S. et al. (2008). "Cyclin-dependent kinase 9: a key transcriptional regulator and potential drug target in oncology, virology and cardiology," *Trends in Pharmacological Sciences* 29(6): 302-313.
Wang, S. et al. (2010). "Discovery and Characterization of 2-Anilino-4-(Thiazol-5-yl)Pyrimidine Transcriptional CDK Inhibitors as Anticancer Agents," *Chemistry & Biology* 17: 1111-1121.
Yang, Z. et al. (Aug. 19, 2005). "Recruitment of P-TEFb for Stimulation of Transcriptional Elongation by the Bromodomain Protein Brd4," *Molecular Cell* 19: 535-545.
Zhou, M. et al. (Dec. 2004). "Coordination of Transcription Factor Phosphorylation and Histone Methylation by the P-TEFb Kinase during Human Immunodeficiency Virus Type 1 Transcription," *Journal of Virology* 78(24): 13522-13533.
Zhou, Q. et al. (Sep. 2006). "The Yin and Yang of P-TEFb Regulation: Implications for Human Immunodeficiency Virus Gene Expression and Global Control of Cell Growth and Differentiation," *Microbiology and Molecular Biology Reviews* 70(3): 646-659.

SULFOXIMINE SUBSTITUTED 5-FLUORO-N-(PYRIDIN-2-YL)PYRIDIN-2-AMINE DERIVATIVES AND THEIR USE AS CDK9 KINASE INHIBITORS

CROSS REFERENCE TO RELATED APPLICATIONS

This application is the National Phase application under 35 U.S.C. §371 of International Application No. PCT/EP2014/064184, filed Jul. 3, 2014, which claims the benefit of European Application No. 13175067.1, filed Jul. 4, 2013, the disclosures of each of which are hereby incorporated by reference in their entireties.

The present invention relates to 5-fluoro-N-(pyridin-2-yl) pyridin-2-amine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acteylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 repliction at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO 2009118567 discloses pyrimidine and [1,3,5]triazine derivatives as protein kinase inhibitors, in particular CDK2, CDK7 and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors.

EP1218360 B1, which corresponds to US2004116388A1, US7074789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heteroaryl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO 2011077171 discloses 4,6-disubstituted aminopyrimidine derivatives as inhibitors of CDK9.

WO 2014031937 discloses 4,6-disubstituted aminopyrimidine derivatives as inhibitors of CDK9.

WO 2013037896 discloses disubstituted 5-fluoropyrimidines as selective inhibitors of CDK9.

WO 2013037894 discloses disubstituted 5-fluoropyrimidine derivatives containing a sulfoximine group as selective inhibitors of CDK9.

WO 2014060376 discloses substituted 4-(ortho)-fluorophenyl-5-fluoropyrimidin-2-yl amine derivatives containing a sulfone group as selective inhibitors of CDK9.

WO 2014060375 discloses substituted 5-fluoro-N-(pyridin-2-yl)pyridin-2-amine derivatives containing a sulfone group as selective inhibitors of CDK9.

WO 2014060493 discloses substituted N-(pyridin-2-yl)pyrimidin-4-amine derivatives containing a sulfone group as selective inhibitors of CDK9.

WO 2014076028 discloses substituted 4-(ortho)-fluorophenyl-5-fluoropyrimidin-2-yl amine derivatives containing a sulfoximine group as selective inhibitors of CDK9.

WO 2014076091 discloses substituted 5-fluoro-N-(pyridin-2-yl)pyridin-2-amine derivatives containing a sulfoximine group as selective inhibitors of CDK9.

WO 2014076111 discloses substituted N-(pyridin-2-yl)pyrimidin-4-amine derivatives containing a sulfoximine group as selective inhibitors of CDK9.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to US7618968B2, US7291616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as INK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

WO2012142329 concerns amino-pyrimidine compounds as inhibitors of TBKL and/or IKK epsilon.

WO2012139499 discloses urea substituted anilino-pyrimidines as inhibitors of various protein kinases.

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
  improved activity and/or efficacy
  beneficial kinase selectivity profile according to the respective therapeutic need
  improved side effect profile, such as fewer undesired side effects, lower intensity of side effects, or reduced (cyto)toxicity
  improved physicochemical properties, such as solubility in water and body fluids
  improved pharmacokinetic properties, allowing e.g. for dose reduction or an easier dosing scheme
  easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines such as HeLa, HeLa-MaTu-ADR, NCI-H460, DU145, Caco-2, B16F10, A2780 or MOLM-13, compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines such as HeLa, HeLa-MaTu-ADR, NCI-H460, DU145, Caco-2, B16F10, A2780 or MOLM-13, and/or which show an increased potency to inhibit CDK9 activity at high ATP concentrations compared to the compounds known from prior art.

The present invention relates to compounds of general formula (I)

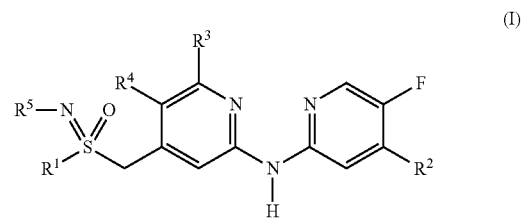

(I)

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
  wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;
$R^2$ represents the group

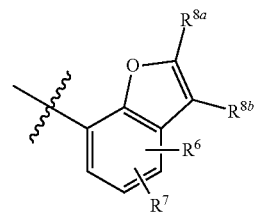

$R^3$, $R^4$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;
$R^5$ represents a group selected from a hydrogen atom, cyano, —C(O)R$^9$, —C(O)OR$^9$, —S(O)$_2$R$^9$, —C(O)NR$^{10}$R$^{11}$, —P(O)(OR$^{12}$)$_2$, —CH$_2$OP(OR$^{12}$)$_2$, $C_1$-$C_6$-alkyl-, $C_3$-$C_7$-cycloalkyl-, heterocyclyl-, phenyl, heteroaryl,
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, halo-$C_1$-$C_3$-alkyl-, $C_3$-$C_7$-cycloalkyl-, heterocyclyl-, phenyl, benzyl or heteroaryl, wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, phenyl, benzyl or heteroaryl, wherein said $C_1$-$C_6$-alkyl-, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

$R^{12}$ represents a group selected from hydrogen, $C_1$-$C_4$-alkyl or benzyl, and the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethanesulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra(n-butyl)ammonium, or N-benzyl-N,N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., 14C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen atom" or "halo" represents fluorine, chlorine, bromine and iodine, particularly chlorine or fluorine, preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_3$-$C_7$-cycloalkyl" is to be understood as preferably meaning a saturated or partially unsaturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring is non-aromatic but can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_5$-cycloalkyl group is a monocyclic hydrocarbon ring such as a cyclopropyl, cyclobutyl, cyclopentyl or cyclohexyl group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. A $C_3$-$C_9$-heterocyclyl is to be understood as meaning a heterocyclyl which contains 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocycliclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly a $C_3$-$C_7$-heterocyclyl is to be understood as meaning a heterocyclyl which contains 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly a $C_3$-$C_6$-heterocyclyl is to be understood as meaning a heterocyclyl which contains 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 7-membered heterocyclic ring"), more particularly said ring can contain 4 or 5 carbon atoms, and 1, 2 or 3 of the above-mentioned heteroatom-containing groups (a "5- to 7-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy-group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy- particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino- for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-t-Butyl-N-methylamino-, N-Ethyl-N-n-pentylamino- and N-n-Hexyl-N-methylamino-.

The term "cyclic amine" is to be understood as preferably meaning a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-" is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferably, halo-$C_1$-$C_3$-alkyl-group is a fluoro-$C_1$-$C_3$-alkyl-group, such as for example —$CF_3$, —$CHF_2$, —$CH_2F$, —$CF_2CF_3$, or —$CH_2CF_3$, more preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl-group to the molecule. Particularly, the "phenyl-$C_1$-$C_3$-alkyl-" is a phenyl-$C_1$-$C_2$-alkyl-, preferably it is a benzyl-group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a"9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl-group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, -a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl-group.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene) sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene) sulfonyloxy, benzenesulfonyloxy, and (4-methoxy-benzene) sulfonyloxy.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$. Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌇ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I),
wherein
$R^1$ represents a group selected from $C_1$-$C_6$-alkyl-, $C_3$-$C_5$-cycloalkyl-,
wherein said group is optionally substituted with one substituent selected from the group of hydroxy, $C_1$-$C_2$-alkoxy-, halo-$C_1$-$C_2$-alkyl-, $C_1$-$C_2$-fluoroalkoxy-, —$NH_2$, alkylamino-, dialkylamino-, cyclic amines, —$OP(O)(OH)_2$, —$C(O)OH$, —$C(O)NH_2$;
$R^2$ represents the group

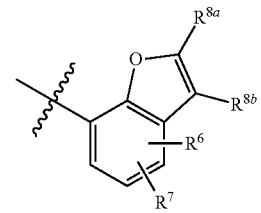

$R^3$ represents a hydrogen atom, a fluoro atom or a chloro atom, a $C_1$-$C_3$-alkyl group or a fluoro-$C_1$-$C_3$-alkyl group;
$R^4$ represents a hydrogen atom or a fluoro atom;
$R^5$ represents a group selected from a hydrogen atom, cyano, —$C(O)R^9$, —$C(O)OR^9$, —$S(O)_2R^9$, —$C(O)NR^{10}R^{11}$, —$P(O)(OR^{12})_2$, —$CH_2OP(OR^{12})_2$, $C_1$-$C_6$-alkyl-, $C_3$-$C_7$-cycloalkyl-, heterocyclyl-, phenyl, heteroaryl,
wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;
$R^9$ represents a group selected from $C_1$-$C_6$-alkyl-, halo-$C_1$-$C_3$-alkyl-, $C_3$-$C_7$-cycloalkyl-, heterocyclyl-, phenyl, benzyl or heteroaryl, wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, benzyl, phenyl or heteroaryl,
wherein said $C_1$-$C_6$-alkyl, $C_3$-$C_7$-cycloalkyl-, heterocyclyl-, benzyl, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

$R^{12}$ represents a group selected from hydrogen or $C_1$-$C_2$-alkyl, and the enantiomers, diastereomers, salts, solvates or salts of solvates thereof.

In a preferred embodiment the present invention concerns compounds of general formula (I),
wherein
$R^1$ represents a $C_1$-$C_6$-alkyl- or $C_3$-$C_5$-cycloalkyl group,
wherein said group is optionally substituted with one substituent selected from the group of hydroxy, $C_1$-$C_6$-alkoxy-, —$NH_2$, alkylamino-, dialkylamino-, cyclic amines, —OP(O)(OH)$_2$;
$R^2$ represents the group

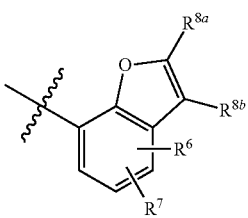

$R^3$ represents a hydrogen atom, fluoro atom or chloro atom, a $C_1$-$C_3$-alkyl group or a fluoro-$C_1$-$C_3$-alkyl group;
$R^4$ represents a hydrogen atom or a fluoro atom;
$R^5$ represents a group selected from a hydrogen atom, cyano, —C(O)$R^9$, —C(O)O$R^9$, —C(O)N$R^{10}R^{11}$, —P(O)(O$R^{12}$)$_2$, —CH$_2$OP(O$R^{12}$)$_2$ or $C_1$-$C_3$-alkyl-,
wherein said $C_1$-$C_3$-alkyl group is optionally substituted with one substituent, selected from —$NH_2$, alkylamino-, dialkylamino-, or cyclic amines;
$R^6$, $R^7$ represent, independently from each other, a group selected from a hydrogen atom, a fluoro atom or a chloro atom;
$R^{8a}$, $R^{8b}$ represent, independently from each other, a group selected from a hydrogen atom, fluoro atom, chloro atom, bromo atom, cyano, methyl-, methoxy-, halo-methyl-, fluoromethoxy-;
$R^9$ represents a group selected from $C_1$-$C_3$-alkyl-, halo-$C_1$-$C_3$-alkyl-, or benzyl group, the phenyl group of which is optionally substituted with one or two substituents, identically or differently, selected from the group of halogen, $C_1$-$C_3$-alkyl-, $C_1$-$C_3$-alkoxy-, —$NH_2$, alkylamino-, dialkylamino-;

$R^{10}$, $R^{11}$ represent, independently from each other, a group selected from hydrogen, $C_1$-$C_3$-alkyl-, benzyl, or $R^{10}$, and $R^{11}$, together with the nitrogen atom they are attached to, form a cyclic amine;

$R^{12}$ represents a group selected from hydrogen or methyl, and the enantiomers, diastereomers, salts, solvates or salts of solvates thereof.

In another preferred embodiment the present invention concerns compounds of general formula (I),
wherein
$R^1$ represents a $C_1$-$C_6$-alkyl group,
wherein said group is optionally substituted with one substituent, selected from the group of $C_1$-$C_3$-alkoxy, —$NH_2$, alkylamino-, dialkylamino-, or cyclic amines;
$R^2$ represents the group

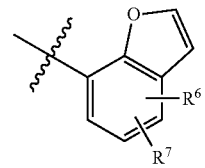

$R^3$ represents a hydrogen atom, fluoro atom or chloro atom or a methyl-, ethyl- or trifluoromethyl-group;
$R^4$ represents a hydrogen atom or fluoro atom;
$R^5$ represents a group selected from a hydrogen atom, cyano, —C(O)$R^9$, —C(O)O$R^9$, —C(O)N$R^{10}R^{11}$;
$R^6$, $R^7$ represent, independently from each other, a group selected from a hydrogen atom, fluoro atom or chloro atom;
$R^9$ represents a $C_1$-$C_3$-alkyl group, a benzyl group, or trifluoromethyl;
$R^{10}$, $R^{11}$ represent, independently from each other, a group selected from hydrogen, $C_1$-$C_2$-alkyl-;
or their enantiomers, diastereomers, salts, solvates or salts of solvates.

In another preferred embodiment the present invention concerns compounds of general formula (I),
wherein
$R^1$ represents a $C_1$-$C_6$-alkyl group,
wherein said group is optionally substituted with one substituent, selected from the group of $C_1$-$C_3$-alkoxy, —$NH_2$, alkylamino-, dialkylamino-, or cyclic amines;
$R^2$ represents the group

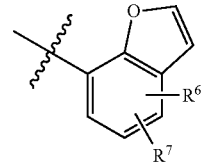

$R^3$ represents a hydrogen atom, fluoro atom or chloro atom or a trifluoromethyl-group;
$R^4$ represents a hydrogen atom or fluoro atom;
$R^5$ represents a group selected from a hydrogen atom, cyano, —C(O)$R^9$, —C(O)O$R^9$, —C(O)N$R^{10}R^{11}$;

$R^6$, $R^7$ represent, independently from each other, a group selected from a hydrogen atom, fluoro atom or chloro atom;
$R^9$ represents a $C_1$-$C_3$-alkyl group, a benzyl group, or trifluoromethyl;
$R^{10}$, $R^{11}$ represent, independently from each other, a group selected from hydrogen, $C_1$-$C_2$-alkyl-;
or their enantiomers, diastereomers, salts, solvates or salts of solvates.

In another particularly preferred embodiment the present invention concerns compounds of general formula (I), wherein
$R^1$ represents a $C_1$-$C_3$-alkyl group;
$R^2$ represents the group

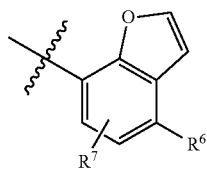

$R^3$ represents a hydrogen atom or fluoro atom or a methyl-, ethyl- or trifluoromethyl-group;
$R^4$ represents a hydrogen atom;
$R^5$ represents a group selected from a hydrogen atom, cyano, —C(O)$R^9$, —C(O)O$R^9$, —C(O)N$R^{10}R^{11}$;
$R^6$ represents a group selected from a hydrogen atom, fluoro atom or chloro atom,
$R^7$ represents a hydrogen atom;
$R^9$ represents a methyl-, ethyl- or trifluoromethyl-group;
$R^{10}$ represents a $C_1$-$C_3$-alkyl group;
$R^{11}$ represents a hydrogen atom;
and the enantiomers, diastereomers, salts, solvates or salts of solvates thereof.

In another particularly preferred embodiment the present invention concerns compounds of general formula (I), wherein
$R^1$ represents a $C_1$-$C_3$-alkyl group;
$R^2$ represents the group

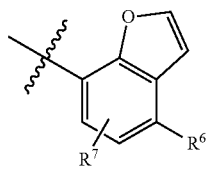

$R^3$ represents a fluoro atom or a trifluoromethyl-group;
$R^4$ represents a hydrogen atom;
$R^5$ represents a group selected from a hydrogen atom, —C(O)$R^9$;
$R^6$ represents a group selected from a hydrogen atom, fluoro atom or chloro atom,
$R^7$ represents hydrogen;
$R^9$ represents a trifluoromethyl-group;
and the enantiomers, diastereomers, salts, solvates or salts of solvates thereof.

In another particularly preferred embodiment the present invention concerns compounds of general formula (I), wherein
$R^1$ represents a methyl group;
$R^2$ represents the group

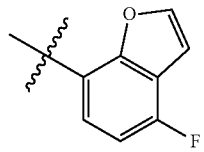

$R^3$ represents a hydrogen atom or fluoro atom or a methyl-, ethyl- or trifluoromethyl-group;
$R^4$ represents a hydrogen atom;
$R^5$ represents a group selected from a hydrogen atom, cyano, —C(O)$R^9$, —C(O)O$R^9$, —C(O)N$R^{10}R^{11}$;
$R^9$ represents a methyl-, ethyl- or trifluoromethyl-group;
$R^{10}$ represents an ethyl-group;
$R^{11}$ represents a hydrogen atom;
and the enantiomers, diastereomers, salts, solvates or salts of solvates thereof.

In another particularly preferred embodiment the present invention concerns compounds of general formula (I), wherein
$R^1$ represents a methyl group;
$R^2$ represents the group

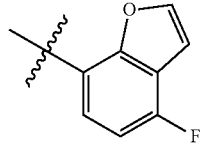 [SMILES: *c1ccc(F)c2ccoc12]

$R^3$ represents a fluoro atom or a trifluoromethyl-group;
$R^4$ represents a hydrogen atom;
$R^5$ represents a group selected from a hydrogen atom, —C(O)$R^9$;
$R^9$ represents a trifluoromethyl-group;
and the enantiomers, diastereomers, salts, solvates or salts of solvates thereof.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —NH$_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a $C_1$-$C_3$-alkyl-, a $C_3$-$C_5$-cycloalkyl-, a 4- to 7-membered heterocyclic ring, a phenyl, a heteroaryl, a phenyl-$C_1$-$C_2$-alkyl- or a heteroaryl-$C_1$-$C_2$-alkyl-group,
wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —NH$_2$, alkylamino-, dialkylamino-, acetylamino-, N-methyl-N-acetylamino-, cyclic amines.

In another embodiment the invention relates to compounds of formula (I), in which $R^1$ represents a group selected from $C_1$-$C_6$-alkyl-, $C_3$-$C_5$-cycloalkyl-,
   wherein said group is optionally substituted with one substituent selected from the group of hydroxy, $C_1$-$C_2$-alkoxy-, halo-$C_1$-$C_2$-alkyl-, $C_1$-$C_2$-fluoroalkoxy-, —$NH_2$, alkylamino-, dialkylamino-, cyclic amines, —OP(O)(OH)$_2$, —C(O)OH, —C(O)NH$_2$.

In another embodiment the invention relates to compounds of formula (I), in which $R^1$ represents a group selected from methyl, ethyl, propan-2-yl, tert butyl, cyclopropyl, cyclohexyl or phenyl,
   wherein said group is optionally substituted with one substituent selected from the group of hydroxy or methoxy.

In another preferred embodiment the invention relates to compounds of formula (I), in which $R^1$ represents a $C_1$-$C_6$-alkyl group,
   wherein said group is optionally substituted with one substituent selected from the group of hydroxy, $C_1$-$C_6$-alkoxy-, —$NH_2$, —OP(O)(OH)$_2$.

In another preferred embodiment the invention relates to compounds of formula (I), in which $R^1$ represents a group selected from methyl, ethyl, propan-2-yl, cyclopropyl, tert-butyl, cyclopentyl, cyclohexyl or phenyl,
   wherein said group is optionally substituted with one substituent, selected from the group of $C_1$-$C_3$-alkoxy, —$NH_2$, alkylamino-, dialkylamino-, or cyclic amines.

In a particularly preferred embodiment the present invention concerns compounds of general formula (I), wherein $R^1$ represents a $C_1$-$C_3$-alkyl group.

In another particularly preferred embodiment the present invention concerns compounds of general formula (I), wherein $R^1$ represents a methyl group.

In another embodiment the invention relates to compounds of formula (I), in which $R^2$ represents the group

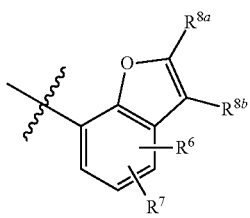

wherein
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^2$ represents the group

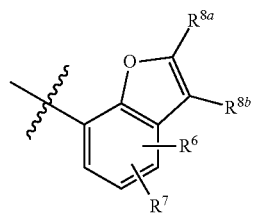

wherein
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^{8a}$, $R^{8b}$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^2$ represents the group

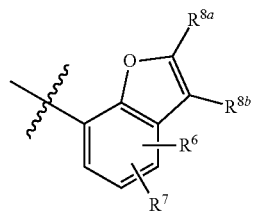

wherein
$R^6$, $R^7$ represent, independently from each other, a group selected from a hydrogen atom, a fluoro atom or a chloro atom;
$R^{8a}$, $R^{8b}$ represent, independently from each other, a group selected from a hydrogen atom, fluoro atom, chloro atom, bromo atom, cyano, methyl-, methoxy-, halo-methyl-, fluoromethoxy-.

In a particularly preferred embodiment the invention relates to compounds of formula (I), in which $R^2$ represents the group

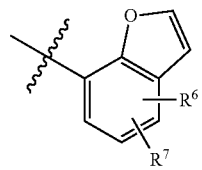

wherein
$R^6$, $R^7$ represent, independently from each other, a group selected from a hydrogen atom, fluoro atom or chloro atom.

In another particularly preferred embodiment the invention relates to compounds of formula (I), in which $R^2$ represents the group

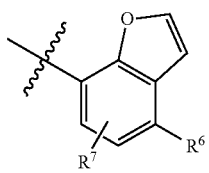

wherein
R⁶ represents a group selected from hydrogen, a fluoro or chloro atom,
R⁷ represents hydrogen.

In another particularly preferred embodiment the invention relates to compounds of formula (I), in which $R^2$ represents the group

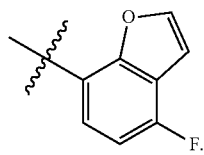 [SMILES: *c1ccc(F)c2ccoc12]

In another embodiment the invention relates to compounds of formula (I), in which $R^3$ and $R^4$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^3$ represents a hydrogen atom, fluoro atom or chloro atom, a $C_1$-$C_3$-alkyl group, or a fluoro-$C_1$-$C_3$-alkyl group, and $R^4$ represents a hydrogen atom or a fluoro atom.

In another preferred embodiment the invention relates to compounds of formula (I), in which $R^3$ represents a hydrogen atom, fluoro atom or chloro atom, or a trifluoromethyl-group, and $R^4$ represents a hydrogen atom or a fluoro atom.

In another preferred embodiment the invention relates to compounds of formula (I), in which $R^3$ represents a hydrogen atom, fluoro atom or chloro atom, or a methyl-, ethyl- or trifluoromethyl-group, and $R^4$ represents a hydrogen atom or a fluoro atom.

In another preferred embodiment the invention relates to compounds of formula (I), in which $R^3$ represents a hydrogen atom, fluoro atom or chloro atom, or a methyl-, ethyl- or trifluoromethyl-group, and $R^4$ represents a hydrogen atom.

In another preferred embodiment the invention relates to compounds of formula (I), in which $R^3$ represents a hydrogen atom or fluoro atom, or a methyl-, ethyl- or trifluoromethyl-group, and $R^4$ represents a hydrogen atom or a fluoro atom.

In another preferred embodiment the invention relates to compounds of formula (I), in which $R^3$ represents a hydrogen atom or fluoro atom, or a methyl-, ethyl- or trifluoromethyl-group, and $R^4$ represents a hydrogen atom.

In another preferred embodiment the invention relates to compounds of formula (I), in which $R^3$ represents a methyl-, ethyl- or trifluoromethyl-group, and $R^4$ represents a hydrogen atom or a fluoro atom.

In another preferred embodiment the invention relates to compounds of formula (I), in which $R^3$ represents a methyl-, ethyl- or trifluoromethyl-group, and $R^4$ represents a hydrogen atom.

In another embodiment the invention relates to compounds of formula (I), in which $R^3$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In a preferred embodiment the invention relates to compounds of formula (I), in which $R^3$ represents a hydrogen atom, a fluoro atom or a chloro atom, a $C_1$-$C_3$-alkyl group or a fluoro-$C_1$-$C_3$-alkyl group.

In another preferred embodiment the invention relates to compounds of formula (I), in which $R^3$ represents a hydrogen atom, fluoro atom or chloro atom, a $C_1$-$C_2$-alkyl group or a fluoro-$C_1$-$C_2$-alkyl group.

In another preferred embodiment the invention relates to compounds of formula (I), in which $R^3$ represents a hydrogen atom, fluoro atom or chloro atom or a trifluoromethyl-group.

In another preferred embodiment the invention relates to compounds of formula (I), in which $R^3$ represents a hydrogen atom, fluoro atom or chloro atom, or a methyl-, ethyl- or trifluoromethyl-group.

In another preferred embodiment the invention relates to compounds of formula (I), in which $R^3$ represents a hydrogen atom, fluoro atom, or a methyl-, ethyl- or trifluoromethyl-group.

In another preferred embodiment the invention relates to compounds of formula (I), in which $R^3$ represents a methyl-, ethyl- or trifluoromethyl-group.

In another preferred embodiment the invention relates to compounds of formula (I), in which $R^3$ represents a methyl- or ethyl-group.

In another preferred embodiment the invention relates to compounds of formula (I), in which $R^3$ represents a methyl- or trifluoromethyl-group.

In another preferred embodiment the invention relates to compounds of formula (I), in which $R^3$ represents an ethyl- or trifluoromethyl-group.

In another preferred embodiment the invention relates to compounds of formula (I), in which $R^3$ represents a fluoro atom.

In another preferred embodiment the invention relates to compounds of formula (I), in which $R^3$ represents a trifluoromethyl-group.

In another preferred embodiment the invention relates to compounds of formula (I), in which $R^3$ represents a methyl-group.

In another preferred embodiment the invention relates to compounds of formula (I), in which $R^3$ represents an ethyl-group.

In another embodiment the invention relates to compounds of formula (I), in which $R^4$ represents a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^4$ represents a group selected from a hydrogen, a fluoro or a chloro atom.

In a preferred embodiment the invention relates to compounds of formula (I), in which $R^4$ represents a group selected from a hydrogen atom or fluoro atom.

In another preferred embodiment the invention relates to compounds of formula (I), in which $R^4$ represents a fluoro atom.

In a particularly preferred embodiment the invention relates to compounds of formula (I), in which $R^4$ represents a hydrogen atom.

In another embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(O$R^{12}$)$_2$, —CH$_2$OP(O$R^{12}$)$_2$, $C_1$-$C_6$-alkyl-, $C_3$-$C_7$-cycloalkyl-, heterocyclyl-, phenyl, heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$, —P(O)(O$R^{12}$)$_2$, —CH$_2$OP(O$R^{12}$)$_2$ or $C_1$-$C_3$-alkyl-,
wherein said $C_1$-$C_3$-alkyl group is optionally substituted with one substituent, selected from —NH$_2$, alkylamino-, dialkylamino-, or cyclic amines.

In a preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$.

In another preferred embodiment the invention relates to compounds of formula (I), in which $R^5$ represents a group selected from a hydrogen atom or cyano.

In another preferred embodiment the invention relates to compounds of formula (I), in which $R^5$ represents a group selected from a hydrogen atom, —C(O)O$R^9$ or —C(O)N$R^{10}R^{11}$.

In another preferred embodiment the invention relates to compounds of formula (I), in which $R^5$ represents a group selected from a hydrogen atom or —C(O)N$R^{10}R^{11}$.

In another preferred embodiment the invention relates to compounds of formula (I), in which $R^5$ represents a group selected from a hydrogen atom or —C(O)O$R^9$.

In another preferred embodiment the invention relates to compounds of formula (I), in which $R^5$ represents a group selected from a hydrogen atom, cyano, —C(O)O$R^9$, —C(O)N$R^{10}R^{11}$.

In another preferred embodiment the invention relates to compounds of formula (I), in which $R^5$ represents a cyano group.

In another preferred embodiment the invention relates to compounds of formula (I), in which $R^5$ represents a —C(O)$R^9$ group.

In another preferred embodiment the invention relates to compounds of formula (I), in which $R^5$ represents a —C(O)O$R^9$ group.

In another preferred embodiment the invention relates to compounds of formula (I), in which $R^5$ represents a —C(O)N$R^{10}R^{11}$ group.

In a particularly preferred embodiment the invention relates to compounds of formula (I), in which $R^5$ represents a group selected from a hydrogen atom or —C(O)$R^9$.

In another particularly preferred embodiment the invention relates to compounds of formula (I), in which $R^5$ represents a hydrogen atom.

In another particularly preferred embodiment the invention relates to compounds of formula (I), in which $R^5$ represents —C(O)$R^9$.

In another embodiment the invention relates to compounds of formula (I), in which $R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from a hydrogen atom, a fluoro atom or a chloro atom.

In another embodiment the invention relates to compounds of formula (I), in which $R^6$ and $R^7$ represent, independently from each other, a group selected from a hydrogen or fluoro atom.

In a particularly preferred embodiment the invention relates to compounds of formula (I), in which $R^6$ represents hydrogen, para-fluoro, or para-chloro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents para-fluoro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents para-fluoro, whereby para refers to the point of attachment of $R^2$ to the rest of the molecule.

In a particularly preferred embodiment the invention relates to compounds of formula (I), in which $R^7$ represents a hydrogen atom.

In another embodiment the invention relates to compounds of formula (I), in which $R^{8a}$, $R^{8b}$ represent, independently from each other, a group selected from hydrogen, a fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^{8a}$, $R^{8b}$ represent, independently from each other, a group selected from hydrogen, a fluoro atom, chloro atom, bromo atom, cyano, methyl-, methoxy-, halo-methyl-, fluoromethoxy-.

In another embodiment the invention relates to compounds of formula (I), in which $R^9$ represents a group selected from $C_1$-$C_6$-alkyl-, $C_1$-$C_3$-haloalkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^9$ represents a group selected from $C_1$-$C_3$-alkyl-, $C_1$-$C_3$-haloalkyl, benzyl group, the phenyl group of which is optionally substituted with one or two substituents, identically or differently, selected from the group of halogen, $C_1$-$C_3$-alkyl-, $C_1$-$C_3$-alkoxy-, —NH$_2$, alkylamino-, dialkylamino-.

In another preferred embodiment the invention relates to compounds of formula (I), in which $R^9$ represents a group selected from $C_1$-$C_3$-alkyl-, benzyl, or trifluoromethyl.

In another preferred embodiment the invention relates to compounds of formula (I), in which $R^9$ represents a group selected from methyl-, ethyl- or trifluoromethyl-.

In another preferred embodiment the invention relates to compounds of formula (I), in which $R^9$ represents a group selected from methyl- or ethyl-.

In another preferred embodiment the invention relates to compounds of formula (I), in which $R^9$ represents a group selected from methyl- or trifluoromethyl-.

In another preferred embodiment the invention relates to compounds of formula (I), in which $R^9$ represents a group selected from ethyl- or trifluoromethyl.

In a particularly preferred embodiment the invention relates to compounds of formula (I), in which $R^9$ represents a trifluoromethyl group.

In another embodiment the invention relates to compounds of formula (I), in which $R^{10}$, $R^{11}$ represent, independently from each other, a group selected from hydrogen, $C_1$-$C_6$-alkyl-, $C_3$-$C_7$-cycloalkyl-, heterocyclyl-, phenyl, benzyl or heteroaryl,
wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine.

In a preferred embodiment the invention relates to compounds of formula (I), in which $R^{10}$ and $R^{11}$ represent, independently from each other, a group selected from hydrogen, $C_1$-$C_3$-alkyl-, benzyl, or $R^{10}$ and $R^{11}$, together with the nitrogen atom they are attached to, form a cyclic amine.

In another preferred embodiment the invention relates to compounds of formula (I), in which $R^{10}$ and $R^{11}$ represent, independently from each other, a group selected from hydrogen or $C_1$-$C_2$-alkyl-.

In another preferred embodiment the invention relates to compounds of formula (I), in which $R^{10}$ and $R^{11}$ represent, independently from each other, hydrogen or a $C_1$-$C_6$-alkyl-.

In a particularly preferred embodiment the invention relates to compounds of formula (I), in which $R^{10}$ and $R^{11}$ represent hydrogen.

In another particularly preferred embodiment the invention relates to compounds of formula (I), in which $R^{10}$ represents a $C_1$-$C_2$-alkyl-group, and $R^{11}$ represents a hydrogen atom.

In another particularly preferred embodiment the invention relates to compounds of formula (I), in which $R^{10}$ represents an ethyl-group, and $R^{11}$ represents a hydrogen atom.

In another particularly preferred embodiment the invention relates to compounds of formula (I), in which $R^{10}$ represents a methyl-group, and $R^{11}$ represents a hydrogen atom.

In a preferred embodiment the invention relates to compounds of formula (I), in which $R^{10}$ represents a group selected from hydrogen, $C_1$-$C_3$-alkyl-, benzyl.

In another preferred embodiment the invention relates to compounds of formula (I), in which $R^{10}$ represents a $C_1$-$C_2$-alkyl-group.

In a particularly preferred embodiment the invention relates to compounds of formula (I), in which $R^{10}$ represents hydrogen.

In another preferred embodiment the invention relates to compounds of formula (I), in which $R^{11}$ represents a group selected from hydrogen or $C_1$-$C_2$-alkyl.

In a particularly preferred embodiment the invention relates to compounds of formula (I), in which $R^{11}$ represents hydrogen.

In another embodiment the invention relates to compounds of formula (I), in which $R^{12}$ represents a group selected from hydrogen, $C_1$-$C_4$-alkyl or benzyl.

In a preferred embodiment the invention relates to compounds of formula (I), in which $R^{12}$ represents a group selected from hydrogen or $C_1$-$C_2$-alkyl.

In another preferred embodiment the invention relates to compounds of formula (I), in which $R^{12}$ represents a group selected from hydrogen or methyl.

In another preferred embodiment the invention relates to compounds of formula (I), in which $R^{12}$ represents hydrogen.

It is to be understood that the present invention relates to any sub-combination within any embodiment of the present invention of compounds of formula (I), supra.

In another preferred embodiment the invention relates to a specific stereoisomer of compounds of the formula (I) featuring a lower $IC_{50}$ vs CDK9 as compared to other stereoisomers of the respective compound, determined according to Method 1a described in the Materials and Methods section below.

In another preferred embodiment the invention relates to a specific stereoisomer of compounds of the formula (I) featuring a lower $IC_{50}$ vs CDK9 at high ATP concentration as compared to other stereoisomers of the respective compound, determined according to Method 1b described in the Materials and Methods section below.

In another preferred embodiment the invention relates to a specific stereoisomer of compounds of the formula (I) featuring a higher selectivity in favor of CDK9 over CDK2 as compared to other stereoisomers of the respective compound, determined according to Methods 1a (CDK9) and 2 (CDK2) described in the Materials and Methods section below.

In another preferred embodiment the invention relates to a specific stereoisomer of compounds of the formula (I) featuring a higher anti-proliferative activity in tumor cell lines such as HeLa as compared to other stereoisomers of the respective compound, determined according to Method 3 described in the Materials and Methods section below.

In another preferred embodiment the invention relates to a specific stereoisomer of compounds of the formula (I) featuring a higher anti-proliferative activity in tumor cell lines such as HeLa, HeLa-MaTu-ADR, NCI-H460, DU145, Caco-2, B16F10, A2780 or MOLM-13, as compared to other stereoisomers of the respective compound, determined according to Method 3 described in the Materials and Methods section below.

In another preferred embodiment the invention relates to a specific stereoisomer of compounds of the formula (I) featuring a higher an increased apparent Caco-2 permeability ($P_{app}$ A-B) across Caco-2 cell monolayers compared to other stereoisomers of the respective compound, determined according to Method 4 described in the Materials and Methods section below.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds:

(rac)-5-Fluoro-4-(4-fluoro-1-benzofuran-7-yl)-N-{6-fluoro-4-[(S-methylsulfonimidoyl)methyl]pyridin-2-yl}pyridin-2-amine (rac)-2,2,2-Trifluoro-N-{[(2-fluoro-6-{[5-fluoro-4-(4-fluoro-1-benzofuran-7-yl)pyridin-2-yl]amino}pyridin-4-yl)methyl](methyl)oxido-λ⁶-sulfanylidene}acetamide (rac)-5-Fluoro-4-(4-fluoro-1-benzofuran-7-yl)-N-{4-[(S-methylsulfonimidoyl)methyl]-6-(trifluoromethyl)pyridin-2-yl}pyridin-2-amine (rac)-2,2,2-Trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)oxido-λ⁶-sulfanylidene]acetamide (rac)-5-Fluoro-4-(4-fluoro-1-benzofuran-7-yl)-N-{4-[(S-methylsulfonimidoyl)methyl]pyridin-2-yl}pyridin-2-amine (rac)-2,2,2-Trifluoro-N-{[(2-{[5-fluoro-4-(4-fluoro-1-benzofuran-7-yl)pyridin-2-yl]amino}pyridin-4-yl)methyl](methyl)oxido-λ⁶-sulfanylidene}acetamide (rac)-5-Fluoro-4-(4-fluoro-1-benzofuran-7-yl)-N-{6-methyl-4-[(S-methylsulfonimidoyl)methyl]pyridin-2-yl}pyridin-2-amine (rac)-N-{6-Ethyl-4-[S-methylsulfonimidoyl)-methyl]pyridin-2-yl}-5-fluoro-4-(4-fluoro-1-benzofuran-7-yl)pyridin-2-amine (rac)-{[(2-{[5-fluoro-4-(4-fluoro-1-benzofuran-7-yl)pyridin-2-yl]amino}pyridin-4-yl)methyl](methyl)oxido-λ⁶-sulfanylidene}cyanamide (rac)-N-{[(2-{[5-fluoro-4-(4-fluoro-1-benzofuran-7-yl)pyridin-2-yl]amino}pyridin-4-yl)methyl](methyl)oxido-λ⁶-sulfanylidene}acetamide (rac)-Ethyl {[(2-{[5-fluoro-4-(4-fluoro-1-benzofuran-7-yl)pyridin-2-yl]amino}pyridin-4-yl)methyl](methyl)oxido-λ⁶-sulfanylidene}carbamate (rac)-1-Ethyl-3-{[(2-{[5-fluoro-4-(4-fluoro-1-benzofuran-7-yl)pyridin-2-yl]amino}pyridin-4-yl)methyl](methyl)oxido-λ⁶-sulfanylidene}urea (rac)-1-{[(2-{[5-Fluoro-4-(4-fluoro-1-benzofuran-7-yl)pyridin-2-yl]amino}pyridin-4-yl)methyl](methyl)oxido-λ⁶-sulfanylidene}-3-(2,2,2-trifluoroethyl)urea (+)-5-Fluoro-4-(4-fluoro-1-benzofuran-7-yl)-N-{4-[(S-methylsulfonimidoyl)methyl]pyridin-2-yl}pyridin-2-amine (−)-5-Fluoro-4-(4-fluoro-1-benzofuran-7-yl)-N-{4-[(S-methylsulfonimidoyl)methyl]pyridin-2-yl}pyridin-2-amine or their enantiomers, diastereomers, salts, solvates or salts of solvates.

The above mentioned definitions of radicals which have been detailed in general terms or in preferred ranges also apply to the end products of the formula (I) and, analogously, to the starting materials or intermediates required in each case for the preparation.

The invention furthermore relates to a process for the preparation of the compounds of formula (I) according to the invention, in which N-unprotected sulfoximines of formula (I), in which $R^5$ represents hydrogen, are reacted with suitable agents to give N-functionalized sulfoximines of formula (I), in which $R^5$ is as defined for the compound of formula (I) according to the invention but is different from hydrogen,

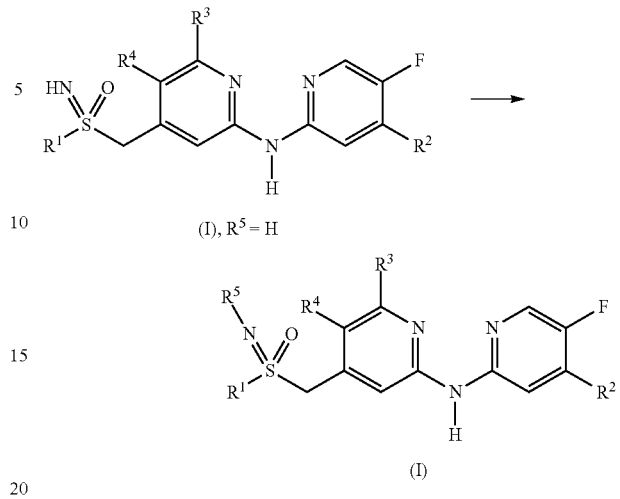

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (6), in which method compounds of formula (5), in which $R^1$, $R^2$, $R^3$, and $R^4$ are as defined for the compound of the formula (I) according to the present invention,

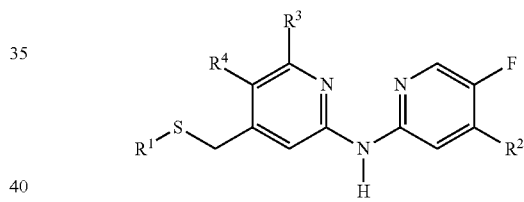

are reacted with trifluoroacetamide and 1,3-dibromo-5,5-dimethylhydantoin in the presence of an alkali alkoxide as a base in a cyclic ether as a solvent, to give compounds of the formula (6),

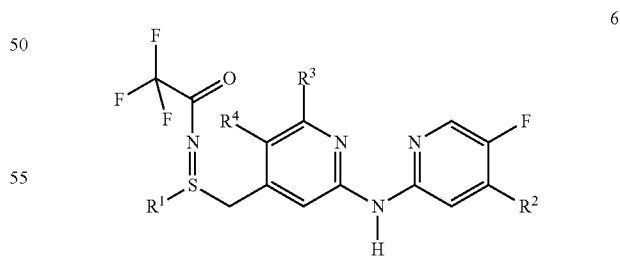

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (6),

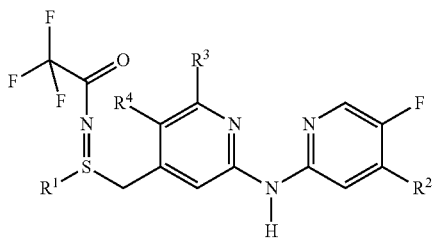

in which $R^1$, $R^2$, $R^3$, and $R^4$ are as defined for the compound of the formula (I) according to the present invention, are oxidised using a peroxomonosulfate based oxidant, at a pH below 11, preferably in the neutral pH range, giving rise to compounds of the formula (I), in which $R^5$ represents trifluoroacetyl-($F_3C$—C(O)—), which can be separated from concomitantly formed NH-sulfoximines, in which $R^5$ stands for hydrogen, by means of chromatography, and in which method complete cleavage of said trifluoroacetyl group can be accomplished by treatment with an alkali or earth alkali carbonate in an alcoholic solvent to give compounds of the formula (I), in which $R^5$ is hydrogen,

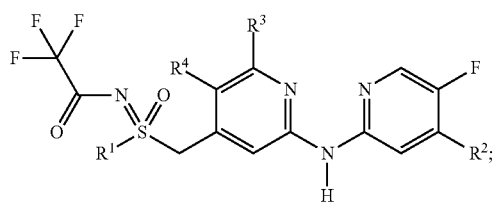

$R^5 =$ —C(O)CF$_3$

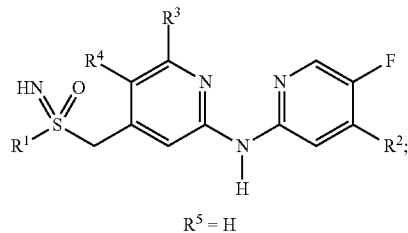

$R^5 = H$ and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (5), in which $R^1$, $R^2$, $R^3$, and $R^4$ are as defined for the compound of the formula (I) according to the present invention,

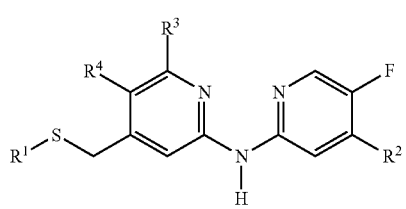

are reacted with trifluoroacetamide and 1,3-dibromo-5,5-dimethylhydantoin in the presence of an alkali alkoxide as a base in a cyclic ether as a solvent, to give compounds of the formula (6),

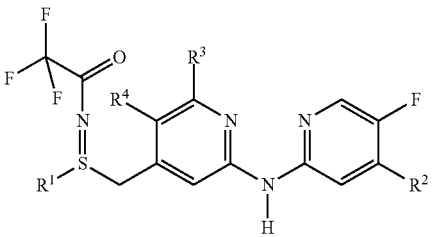

and in which method subsequently said compounds of the formula (6) are oxidised using a peroxomonosulfate based oxidant at a pH below 11, preferably in the neutral pH range, giving rise to compounds of the formula (I), in which $R^5$ represents trifluoroacetyl-($F_3C$—C(O)—), which can be separated from concomitantly formed NH-sulfoximines, in which $R^5$ stands for hydrogen, by means of chromatography, and in which method complete cleavage of said trifluoroacetyl group can be accomplished by treatment with an alkali or earth alkali carbonate in an alcoholic solvent to give compounds of the formula (I), in which $R^5$ is hydrogen,

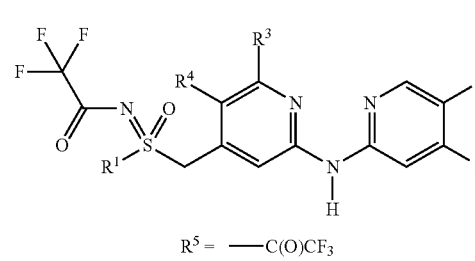

$R^5 =$ —C(O)CF$_3$

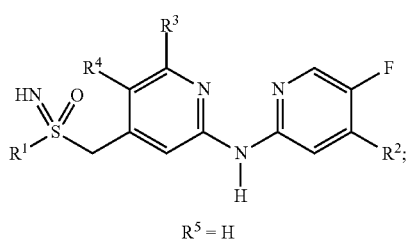

$R^5 = H$ and in which method the resulting compounds are optionally, if appropriate, converted with the corresponding (i) solvents and/or (ii) bases or acids to the solvates, salts and/or solvates of the salts thereof.

The invention further relates to compounds of the formula (5), in which $R^1$, $R^2$, $R^3$ and $R^4$ are as defined for the compounds of formula (I) according to the present invention,

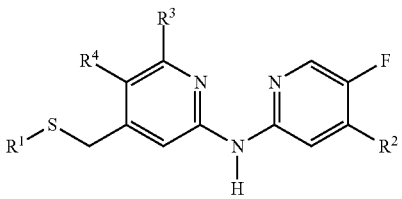

and the salts, solvates or salts of solvates thereof.

The invention further relates to compounds of the formula (6), in which $R^1$, $R^2$, $R^3$ and $R^4$ are as defined for the compounds of formula (I) according to the present invention,

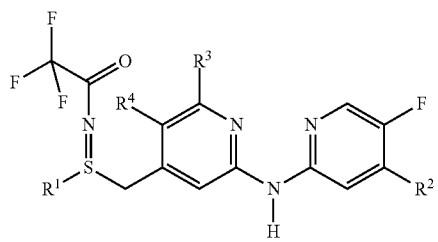

and the enantiomers, diastereomers, salts, solvates or salts of solvates thereof.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as the enantiomers, diastereomers, salts, solvates and salts of solvates thereof are used as inhibitors for CDK9. Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as the enantiomers, diastereomers, salts, solvates and salts of solvates thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Further, preferred compounds of the present invention according to formula (I) show an improved anti-proliferative activity in tumor cell lines such as HeLa, HeLa-MaTu-ADR, NCI-H460, DU145, Caco-2, B16F10, A2780 or MOLM-13, compared to the CDK9 inhibitors described in the prior art.

In context of the present invention, the anti-proliferative activity in tumor cell lines such as HeLa, HeLa-MaTu-ADR, NCI-H460, DU145, Caco-2, B16F10, A2780 or MOLM-13, is preferably determined according to Method 3. ("Proliferation Assay") as described in the Materials and Method section below.

Further, preferred compounds of the present invention according to formula (I) surprisingly show an increased solubility in water at pH 6.5 compared to the compounds described in the prior art.

In context of the present invention the solubility in water at pH 6.5 is preferably determined according to Method 4. ("Equilibrium Shake Flask Solubility Assay") described in the Materials and Method section below.

Further, preferred compounds of the present invention according to formula (I) are characterized by improved pharmacokinetic properties, such as an increased apparent Caco-2 permeability ($P_{app}$ A-B) across Caco-2 cell monolayers, compared to the compounds known from the prior art.

Further, preferred compounds of the present invention according to formula (I) are characterized by improved pharmacokinetic properties, such as a decreased efflux ratio (efflux ratio=$P_{app}$ B-A/$P_{app}$ A-B) from the basal to apical compartment across Caco-2 cell monolayers, compared to the compounds known from the prior art.

In context of the present invention, the apparent Caco-2 permeability values from the basal to apical compartment ($P_{app}$ A-B) or the efflux ratio (defined as the ratio (($P_{app}$ B-A)/($P_{app}$ A-B)) are preferably determined according to Method 5. ("Caco-2 Permeation Assay") described in the Materials and Method section below.

Further, preferred compounds of the present invention according to formula (I) show no significant inhibition of carbonic anhydrase-1 or -2 ($IC_{50}$ values of more than 10 μM)

and therefore show an improved side effect profile as compared to those CDK inhibitors described in the prior art containing a sulfonamide group, which inhibit carbonic anhydrase-1 or -2. In context of the present invention, the carbonic anhydrase-1 and -2 inhibition is preferably determined according to Method 6. ("Carbonic anhydrase Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity auch as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways. The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypothalamic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers. Anal gland adenocarcinomas, mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. mast cell tumors.

Head-and-neck cancers include, but are not limited to laryngeal, hypopharyngeal, nasopharyngeal, oropharyngeal cancer, lip and oral cavity cancer, and squamous cell cancer. Oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma. Malignant histiocytosis, fibrosarcoma, hemangiosarcoma, hemangiopericytoma, leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention as a medicament.

A further subject matter of the present invention is the use of the compounds of general formula (I) according to the invention for the treatment and/or prophylaxis of disorders, in particular of the disorders mentioned above.

A preferred subject matter of the present invention is the use of the compounds of general formula (I) according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use as a medicament.

A further subject matter of the present invention are the compounds according to the invention for the treatment and/or prophylaxis of the disorders mentioned above.

A preferred subject matter of the present invention are the compounds according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds according to the invention for the use in a method for the treatment and/or prophylaxis of the disorders mentioned above.

A preferred subject matter of the present invention are the compounds according to the invention for the use in a method of treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias using an effective amount of the compounds according to the invention.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Another aspect of the present invention relates to the use of the pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Another aspect of the present invention relates to pharmaceutical combinations and/or the pharmaceutical compositions according to the invention for the treatment and/or prophylaxis of disorders, in particular of the disorders mentioned above.

Another aspect of the present invention relates to pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CyeT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium orthovanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

1b. CDK9/CyeT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium orthovanadate, 0.01% (v/v) Nonidet-P40 (Sigma)] were added and the mixture was incubated for 15 mM at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 mM at 22° C. The concentration of CDK9/CycT1 was adjusted depending of the activity of the enzyme lot and was chosen appropriate to have the assay in the linear range, typical concentrations were in the range of 0.5 µg/mL The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077])

in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 µM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL. The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 µM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 µL of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.001-10 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The $IC_{50}$ values (inhibitory concentration at 50% of maximal effect) were determined by means of a 4 parameter fit.

Non-adherent MOLM-13 human acute myeloid leukemia cells (DSMZ ACC 554) were seeded at a density of 5,000 cells/well in a 96-well multititer plate in 100 µL of growth medium supplemented 10% fetal calf serum. After 24 hours, cell viability of one plate (zero-point plate) was determined with the Cell Titre-Glo Luminescent Cell Viability Assay (Promega), while 50 µL of test compound containing medium was added to the wells of the other plates (final concentrations in the range of 0.001-10 μM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

The substances were tested in the following cell lines which represent the stated indications in an exemplary manner:

| Cell line | Source | Indication |
|---|---|---|
| B16F10 | ATCC | melanomas |
| HeLa | ATCC | cervical carcinomas |
| NCI-H460 | ATCC | non-small cell lung carcinomas |
| A2780 | ECACC | ovarian carcinomas |
| DU 145 | ATCC | hormone-independent human prostate carcinomas |
| HeLa-MaTu-ADR | EPO-GmbH | multidrug-resistant human cervical carcinomas |
| Caco-2 | ATCC | colorectal carcinomas |
| MOLM-13 | DSMZ | acute myeloid leukemias |

PREPARATIVE EXAMPLES

Syntheses of Compounds

The syntheses of the 5-fluoro-N-(pyridin-2-yl)pyridin-2-amine derivatives according to the present invention are preferably carried out according to the general synthetic sequence, shown in Scheme 1.

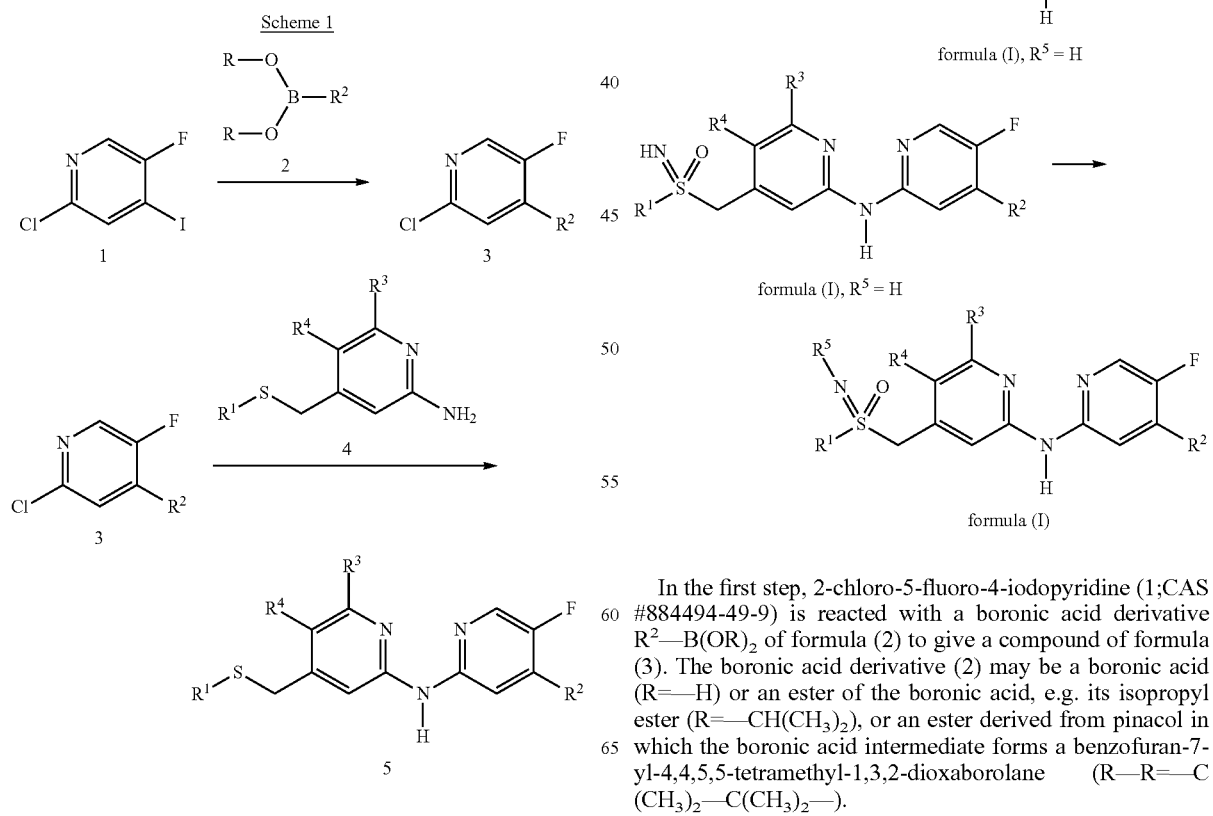

In the first step, 2-chloro-5-fluoro-4-iodopyridine (1;CAS #884494-49-9) is reacted with a boronic acid derivative $R^2$—$B(OR)_2$ of formula (2) to give a compound of formula (3). The boronic acid derivative (2) may be a boronic acid (R═—H) or an ester of the boronic acid, e.g. its isopropyl ester (R═—$CH(CH_3)_2$), or an ester derived from pinacol in which the boronic acid intermediate forms a benzofuran-7-yl-4,4,5,5-tetramethyl-1,3,2-dioxaborolane (R—R═—C($CH_3$)$_2$—C($CH_3$)$_2$—).

The coupling reaction is catalyzed by palladium catalysts, e.g. by Pd(O) catalysts like tetrakis(triphenylphosphine)palladium(0) [Pd(PP$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate (review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

In the second step, a compound of formula (3) is reacted with a suitable pyridin-2-amine of formula (4), in which R$^1$, R$^3$ and R$^4$ are as defined for the compound of general formula (I), to give a compound of formula (5). Said pyridine-2-amines of the formula (4) can be prepared from commercially available starting materials well known to the person skilled in the art, such as suitable pyridine-4-carboxylic acids, by standard functional group transformations, such as reduction of said carboxylic acid to the corresponding hydroxymethyl group, followed e.g. by chlorination and nucleophilic displacement e.g. with sodium methanethiolate, as described in detail in the Experimental Section, in order to introduce the thioether moiety attached to C-4. The amino group present in compounds of the formula (4) can be introduced e.g. by reaction of a 2,6-difluoropyridine with ammonia (see the Experimental section and WO 2006/076131). The coupling reaction of (3) and (4) can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the herein described use of tris(dibenzylideneacetone)dipalladium(0), (9,9-dimethyl-9H-xanthene-4,5-diyl)bis(diphenylphosphane) and cesium carbonate in dioxane. The reactions are preferably run under argon for 3-48 hours at 100° C. in a microwave oven or in an oil bath.

In the third step, imination of a compound of formula (5) gives the corresponding sulfilimine of formula (6) (see for examples: a) C. Bolm et al, Organic Letters, 2004, 6, 1305; b) J. Krüger et al, WO 2012/038411). Said imination is performed by reacting a compound of the formula (5) with trifluoroacetamide and a suitable oxidant, such as 1,3-dibromo-5,5-dimethylhydantoin, in the presence of a base, such as an alkali alkoxide, preferably sodium tert.-butoxide, in a suitable solvent, such as a cyclic ether e.g. dioxane or tetrahydrofuran.

Oxidation of the sulfilimine of formula (6) optionally followed by deprotection of the trifluoroacetyl group, gives the N-unprotected sulfoximine of formula (I) (see for examples: a) A. Plant et al, WO 2006/037945; b) J. Krüger et al, WO 2012/038411). Said oxidation is performed by reacting compounds of the formula (6), preferably with a peroxomonosulfate based oxidant, such as Oxone® (CAS No. 37222-66-5) at a pH below 11, preferably in the neutral pH range, giving rise to compounds of the formula (I), in which R$^5$ represents trifluoroacetyl (—C(O)CF$_3$), which can be separated from concomitantly formed NH-sulfoximines, in which R$^5$ stands for hydrogen, by means of chromatography, and in which method complete cleavage of said trifluoroacetyl group can be accomplished by treatment with an alkali or earth alkali carbonate, preferably potassium carbonate, in a suitable alcohol, such as an aliphatic alcohol C$_1$-C$_6$-alkyl-OH, preferably methanol. Alternative oxidation methods include, but are not limited to, the use of potassium permanganate in a lower aliphatic ketone such as acetone.

N-unprotected sulfoximines of formula (I) may be reacted to give N-functionalized derivatives of formula (I). There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.

Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.

Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Reaction with cyanogen bromide: see for example: a) D. T. Sauer et al, Inorganic Chemistry 1972, 11, 238; b) C. Bolm et al, Org. Lett. 2007, 9, 2951; c) U. Lücking et al, WO 2011/29537.

Alternatively, intermediates of the formula (5) can be approached, as outlined in Scheme 1a, by reacting intermediates of the formula (3), which are available as outlined supra in Scheme 1, with lithium hexamethyldisilazane to give the corresponding pyridine-2-amines of the formula (3a). Said pyridine-2-amines of the formula (3a) are subsequently reacted with 2-chloropyridines of the formula (4a), in which R$^1$, R$^3$ and R$^4$ are as defined for the compound of general formula (I), in a C—N coupling reaction as described supra for the coupling of compounds of the formulae (3) and (4), to give bis-pyridine amine intermediates of the formula (5), which can be further converted into the compounds of the invention as outlined in Scheme 1. 2-Chloropyridines of the formula (4a) can be prepared from commercially available starting materials, using methods known to the person skilled in the art e.g. as described for the synthesis of compounds of the formula (4) and, in more detail, in the Experimental Section.

Scheme 1a

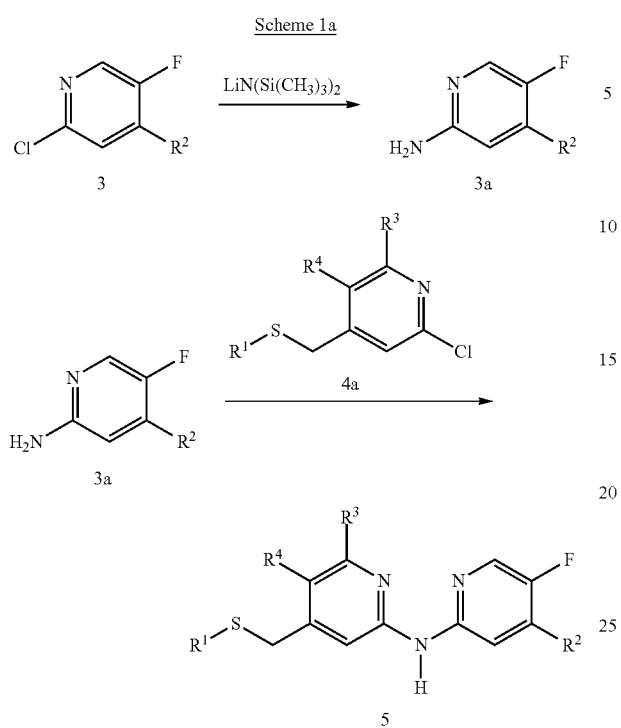

A further alternative synthesis approach to the 5-fluoro-N-(pyridin-2-yl)pyridin-2-amine derivatives according to the present invention is described in Scheme 2.

Scheme 2

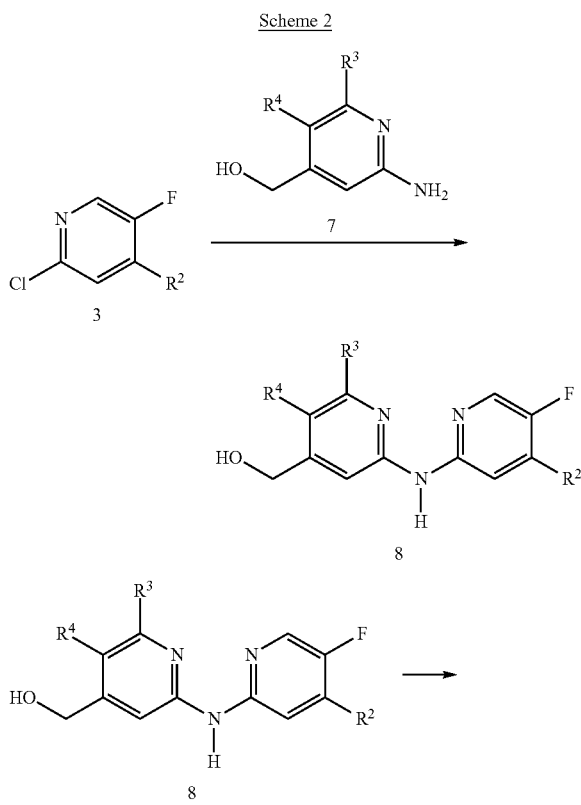

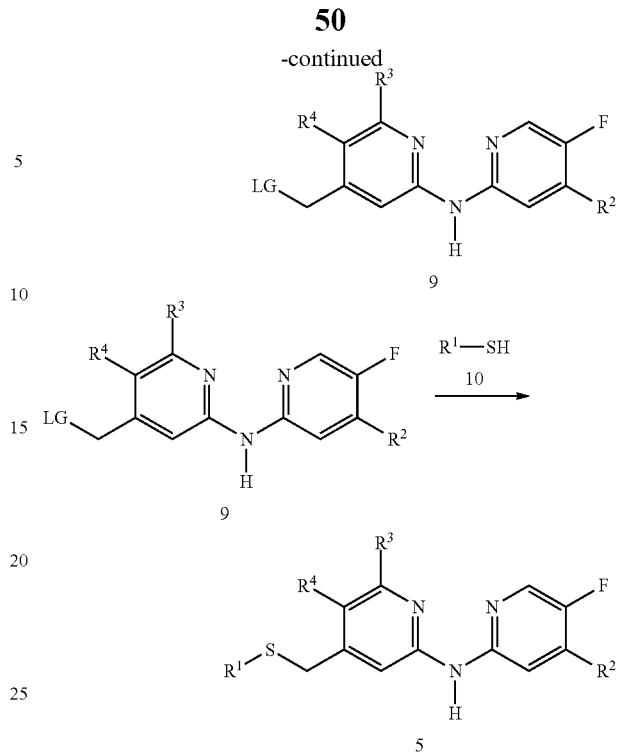

In the first step, a compound of formula (3) in which $R^2$ is as defined for the compound of general formula (I), can be reacted with a suitable pyridin-2-amine of formula (7), in which $R^3$ and $R^4$ are as defined for the compound of general formula (I), to give a compound of formula (8). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004), e.g. using tris(dibenzylideneacetone)dipalladium(0), (9,9-dimethyl-9H-xanthene-4,5-diyl)bis(diphenylphosphane) and cesium carbonate in dioxane.

Pyridine-2-amines of formula (7) are commercially available in certain cases, or can be prepared by methods known to the person skilled in the art, e.g. by reduction of the corresponding carboxylic acids or esters thereof.

In the second step, a compound of formula (8), in which $R^2$, $R^3$ and $R^4$ are as defined for the compound of general formula (I), can be converted to a compound of formula (9), in which $R^2$, $R^3$ and $R^4$ are as defined for the compound of general formula (I) and in which LG represents a leaving group, preferably chloro or bromo, e.g. using thionylchloride in NMP or DMF and DCM for the formation of benzylchloride derivatives (LG=Cl). A possibility for the formation of benzylbromide derivatives (LG=Br) is the use of tetrabromomethane and triphenylphosphane in DCM (see for example: Polla et al, Bioorganic and Medicinal Chemistry, 2004, 12, 1151).

In the third step, a compound of formula (9) can be converted to a thioether of formula (5), in which $R^1$, $R^2$, $R^3$ and $R^4$ are as defined for the compound of general formula (I), by reaction with suitable thiols of formula (10), in which $R^1$ is as defined for the compound of formula (I), under basic conditions, yielding the corresponding thioethers of formula (5) (see for example: Sammond et al, Bioorg. Med. Chem. Lett. 2005, 15, 3519). Thiols of formula (10) are known to the person skilled in the art and are commercially available in considerable variety.

In the final steps, the thioether of formula (5) is converted to the corresponding sulfoximine of formula (I) as described in Scheme 1.

Preparation of Compounds

Abbreviations Used in the Description of the Chemistry and in the Examples that Follow are:

br (broad); CDCl$_3$ (deuterated chloroform); cHex (cyclohexane); d (doublet); DCM (dichloromethane); DIPEA (di-iso-propylethylamine); DME (1,2-dimethoxyethane), DMF (dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NBS (N-bromosuccinimide), NMR (nuclear magnetic resonance); p (pentet); Oxone® (triple salt 2KHSO$_5$*KHSO$_4$*K$_2$SO$_4$), Pd(dppf)Cl$_2$ ([1,1'-bis(diphenylphosphino)ferrocene]-dichloro palladium(II) complex with dichloromethane); iPrOH (iso-propanol); q (quartet); RT (room temperature); s (singlet); sat. aq. (saturated aqueous); SiO$_2$ (silica gel); TFA (trifluoroacetic acid); TFAA (trifluoroacetic anhydride), THF (tetrahydrofuran); tr (triplet).

The IUPAC names of the examples were generated using the program 'ACD/Name batch version 12.01' from ACD LABS.

Example 1

(rac)-5-Fluoro-4-(4-fluoro-1-benzofuran-7-yl)-N-{6-fluoro-4-[(S-methylsulfonimidoyl)methyl]pyridin-2-yl}pyridin-2-amine

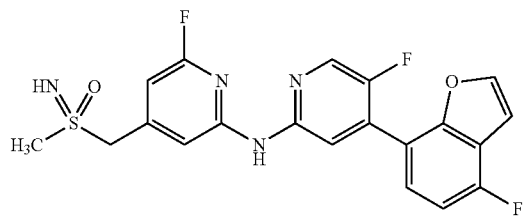 [SMILES: CS(=N)(=O)Cc1cc(F)nc(Nc2cc(-c3ccc(F)c4ccoc34)c(F)cn2)c1]

Example 2

(rac)-2,2,2-Trifluoro-N-{[(2-fluoro-6-{[5-fluoro-4-(4-fluoro-1-benzofuran-7-yl)pyridin-2-yl]amino}pyridin-4-yl)methyl](methyl)oxido-λ$^6$-sulfanylidene}acetamide

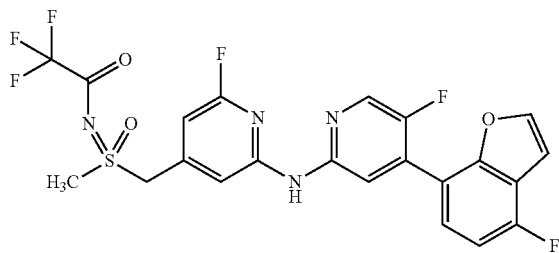 [SMILES: CS(=O)(Cc1cc(F)nc(Nc2cc(-c3ccc(F)c4ccoc34)c(F)cn2)c1)=NC(=O)C(F)(F)F]

Preparation of Intermediate 1.1

2-Chloro-5-fluoro-4-(4-fluoro-1-benzofuran-7-yl)pyridine

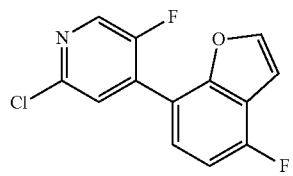 [SMILES: Fc1cnc(Cl)cc1-c1ccc(F)c2ccoc12]

Under an atmosphere of argon, a mixture of 2-chloro-5-fluoro-4-iodopyridine (614 mg; 2.26 mmol; Manchester Organics, CAS #884494-49-9), (4-fluoro-1-benzofuran-7-yl)boronic acid (472 mg; 2.49 mmol; ABCR, CAS #1204580-77-7) and [1,1'-bis(diphenylphosphino)ferrocene]dichloropalladium(II) dichloromethane complex (185 mg; 0.23 mmol; Aldrich Chemical Company Inc.) in an aqueous 2M solution of potassium carbonate (3.39 mL) and 1,2-dimethoxyethane (11.78 mL) was stirred for 90 minutes at 40° C. After cooling, the batch was poured into water and diluted with ethyl acetate. After phase separation the aqueous layer was extracted with ethyl acetate. The combined organic layers were washed with diluted aqueous sodium chloride solution and dried over sodium sulfate. After evaporation the residue was purified by chromatography on silica gel (hexane/dichloromethane) to yield the title compound (257 mg; 0.97 mmol).

$^1$H-NMR (400 MHz, DMSO-d$_6$): δ [ppm]=8.63 (d, 1H), 8.17 (d, 1H), 7.90 (d, 1H), 7.61 (dd, 1H), 7.31 (dd, 1H), 7.22 (d, 1H).

Preparation of Intermediate 1.2

(2,6-Difluoropyridin-4-yl)methanol

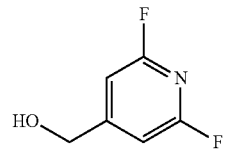

To a stirred solution of 2,6-difluoropyridine-4-carboxylic acid (5.32 g; 32.8 mmol; Matrix Scientific, CAS #88912-23-6) in THF (85 mL) at 0° C. was added a 1M solution of borane-tetrahydrofuran complex in THF (13.2 mL; 131.2 mmol). The mixture was allowed to react at RT overnight. Then, MeOH (15.9 mL) was cautiously added to the stirred mixture while cooling with an ice bath. The batch was diluted with ethyl acetate and washed with aqueous sodium hydroxide solution (1N) and saturated aqueous sodium chloride solution. The organic phase was filtered using a Whatman filter and concentrated to yield the title compound (4.85 g).

$^1$H-NMR (400 MHz, DMSO-d$_6$): δ [ppm]=7.06 (s, 2H), 5.68 (t, 1H), 4.62 (d, 2H).

Preparation of Intermediate 1.3

(2-Amino-6-fluoropyridin-4-yl)methanol

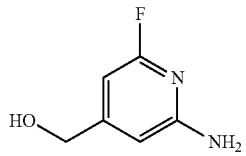

A mixture of (2,6-difluoropyridin-4-yl)methanol (330 mg; 2.27 mmol, intermediate 1.2) and 33% w/w aqueous solution of ammonia (19.8 ml) was placed into a microwave tube. The mixture was allowed to react at 110° C. for 6 hours in the sealed tube under microwave irradiation. Then, the mixture was diluted with water and extracted with ethyl acetate. The combined organic layers were washed with saturated aqueous sodium chloride solution and dried over sodium sulfate. After evaporation the residue was purified by chromatography on silica gel (dichloromethane/methanol) to yield the title compound (209 mg, 1.41 mmol).

$^1$H-NMR (400 MHz, DMSO-$d_6$): δ [ppm]=6.28 (dd, 1H), 6.22 (s, 2H), 5.99 (s, 1H), 5.28 (t, 1H), 4.37 (d, 2H).

Preparation of Intermediate 1.4

4-(Chloromethyl)-6-fluoropyridin-2-amine

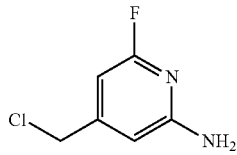

To a stirred solution of (2-amino-6-fluoropyridin-4-yl)methanol (194 mg; 1.36 mmol, intermediate 1.3) in DCM (6.6 ml) and NMP (0.44 ml) at 0° C. was added dropwise thionyl chloride (0.25 mL; 3.41 mmol). The mixture was allowed to react at room temperature overnight. The batch was diluted with aqueous sodium bicarbonate solution and aqueous sodium chloride solution and extracted with DCM (3×). The combined organic phases were filtered, dried over sodium sulfate, and concentrated. The crude material was purified by chromatography on silica gel (dichloromethane/methanol) to yield the desired product (161 mg; 0.94 mmol).

$^1$H-NMR (400 MHz, DMSO-$d_6$): δ [ppm]=6.45 (s, 1H), 6.34 (d, 1H), 6.13 (s, 1H), 4.61 (s, 2H).

Preparation of Intermediate 1.5

6-Fluoro-4-[(methylsulfanyl)methyl]pyridin-2-amine

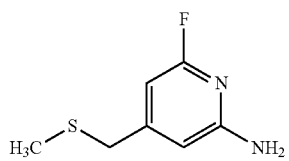

Sodium methanethiolate (99 mg; 1.34 mmol) was added to a stirred solution of 4-(chloromethyl)-6-fluoropyridin-2-amine (110 mg; 0.67 mmol, intermediate 1.4) in ethanol (5.5 mL) at 0° C. The cold bath was removed and the batch was stirred at room temperature for 3 hours. The batch was diluted with saturated aqueous sodium chloride solution and extracted with ethyl acetate (2×). The combined organic phases were washed with water, dried (sodium sulfate), filtered and concentrated to give the desired product (117 mg).

$^1$H-NMR (400 MHz, DMSO-$d_6$): δ [ppm]=6.29 (s, 2H), 6.24 (d, 1H), 6.04 (s, 1H), 3.54 (s, 2H), 1.97 (s, 3H).

Preparation of Intermediate 1.6

5-Fluoro-4-(4-fluoro-1-benzofuran-7-yl)-N-{6-fluoro-4-[(methylsulfanyl)methyl]pyridin-2-yl}pyridin-2-amine

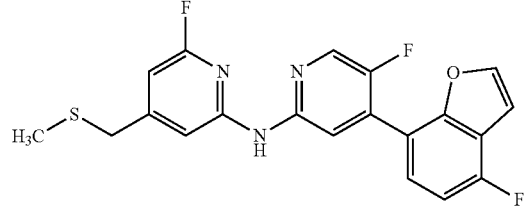 [SMILES: CSCc1cc(F)nc(Nc2cc(-c3ccc(F)c4ccoc34)c(F)cn2)c1]

A mixture of 6-fluoro-4-[(methylsulfanyl)methyl]pyridin-2-amine (206 mg; 1.2 mmol; prepared as described for Intermediate 1.5), 2-chloro-5-fluoro-4-(4-fluoro-1-benzofuran-7-yl)pyridine (255 mg; 0.96 mmol; Intermediate 1.1), chloro(2-dicyclohexylphosphino-2',4',6'-tri-iso-propyl-1,1'-biphenyl)[2-(2-aminoethyl)phenyl]palladium(II) methyl-tert-butylether adduct (79 mg; 0.096 mmol; ABCR GmbH & Co. KG) and 2-(dicyclohexylphosphino)-2',4',6'-triisopropylbiphenyl (45.7 mg; 0.096 mmol; Aldrich Chemical Company Inc.) and potassium phosphate (1.01 g; 4.8 mmol) in toluene (25.4 ml) and NMP (2.5 mL) was stirred under an atmosphere of argon at 130° C. for 3 hours. After cooling, the batch was diluted with ethyl acetate and washed with aqueous sodium chloride solution. The organic phase was filtered using a Whatman filter and concentrated. The residue was purified by chromatography on silica gel (hexane/ethyl acetate) to yield the title compound (295 mg; 0.68 mmol).

$^1$H-NMR (400 MHz, DMSO-$d_6$): δ [ppm]=10.13 (s, 1H), 8.41 (d, 1H), 8.15 (d, 1H), 7.93 (d, 1H), 7.58 (s, 1H), 7.53 (dd, 1H), 7.30 (dd, 1H), 7.21 (d, 1H), 6.53 (s, 1H), 3.71 (s, 2H), 2.02 (s, 3H).

Preparation of Intermediate 1.7

(rac)-2,2,2-Trifluoro-N-[[(2-fluoro-6-{[5-fluoro-4-(4-fluoro-1-benzofuran-7-yl)pyridin-2-yl]amino}pyridin-4-yl)methyl](methyl)-λ$^4$-sulfanylidene]acetamide

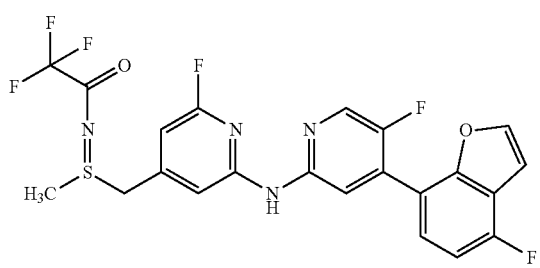 [SMILES: CS(Cc1cc(F)nc(Nc2cc(-c3ccc(F)c4ccoc34)c(F)cn2)c1)=NC(=O)C(F)(F)F]

Under an atmosphere of argon, a solution of 2,2,2-trifluoroacetamide (29 mg; 1.34 mmol) in dioxane (3 mL) was added dropwise to a solution of sodium tert.-butoxide (66.5 mg; 0.67 mmol) in dioxane (3 mL), so that the temperature of the mixture remained below 10° C. Subsequently, a freshly prepared solution of 1,3-dibromo-5,5-dimethylhydantoin (144 mg; 0.5 mmol) in dioxane (3 mL) was added dropwise to the stirred mixture, so that the temperature of the mixture remained below 10° C. Then the mixture was stirred for 10 minutes at ambient temperature. Finally, a solution of 5-fluoro-4-(4-fluoro-1-benzofuran-7-yl)-N-{6-fluoro-4-[(methylsulfanyl)methyl]pyridin-2-yl}pyridin-2-amine (290 mg; 0.67 mmol, intermediate 1.6) in dioxane (3 mL) was added dropwise to the stirred mixture. The mixture was stirred for 30 minutes. The batch was diluted with ethyl acetate and an aqueous solution of sodium sulfite (10%) was added. The batch was extracted with ethyl acetate (3×). The combined organic phases were washed with an aqueous solution of sodium chloride, dried over sodium sulfate and concentrated. The residue was purified by chromatography on silica gel (hexanes/ethyl acetate) to yield the title compound (287 mg; 0.53 mmol).

$^1$H-NMR (400 MHz, DMSO-$d_6$): δ [ppm]=10.30 (s, 1H), 8.39 (d, 1H), 8.16 (d, 1H), 7.87 (d, 1H), 7.69 (s, 1H), 7.54 (dd, 1H), 7.33-7.26 (m, 1H), 7.22 (d, 1H), 6.54 (s, 1H), 4.67-4.44 (m, 2H), 2.82 (s, 3H).

Preparation of End Products

To a solution of (rac)-2,2,2-trifluoro-N-[[(2-fluoro-6-{[5-fluoro-4-(4-fluoro-1-benzofuran-7-yl)pyridin-2-yl]amino}pyridin-4-yl)methyl](methyl)-λ$^4$-sulfanylidene]acetamide (100 mg; 0.183 mmol, intermediate 1.7) in methanol (7 mL) water (0.2 mL) was added a solution of Oxone® (95.8 mg; 0.156 mmol) in water (0.58 mL). The pH was maintained between 6.8 and 7.2 by addition of aqueous solution of potassium hydroxide (5%), if necessary. The mixture was stirred for 60 min Two additional portions of Oxone® (2×45 mg; 2×0.074 mmol) were added after 90 min and 120 min of reaction time. The pH of the mixture was maintained between 6.8 and 7.2 all the time. The reaction mixture was diluted with water and extracted with ethyl acetate (3×). The combined organic phases were washed with an aqueous solution of sodium sulfite (10%), dried over sodium sulfate and concentrated. The residue was purified by chromatography on silica gel (hexanes/ethyl acetate) to yield (rac)-5-fluoro-4-(4-fluoro-1-benzofuran-7-yl)-N-{6-fluoro-4-[(S-methylsulfonimidoyl)methyl]pyridin-2-yl}pyridin-2-amine (17.4 mg; 0.04 mmol; example 1) and (rac)-2,2,2-trifluoro-N-{[(2-fluoro-6-{[5-fluoro-4-(4-fluoro-1-benzofuran-7-yl)pyridin-2-yl]amino}pyridin-4-yl)methyl](methyl)oxido-λ$^4$-sulfanylidene}acetamide (42.8 mg; 0.08 mmol; example 2).

Example 1

$^1$H-NMR (400 MHz, DMSO-$d_6$): δ [ppm]=10.21 (s, 1H), 8.40 (d, 1H), 8.15 (d, 1H), 7.93 (d, 1H), 7.63 (s, 1H), 7.53 (dd, 1H), 7.30 (dd, 1H), 7.21 (d, 1H), 6.64 (s, 1H), 4.45 (s, 2H), 3.87 (br. s., 1H), 2.91 (s, 3H).

Example 2

$^1$H-NMR (400 MHz, DMSO-$d_6$): δ [ppm]=10.35 (s, 1H), 8.39 (d, 1H), 8.16 (d, 1H), 7.88 (d, 1H), 7.78 (s, 1H), 7.54 (dd, 1H), 7.31 (dd, 1H), 7.22 (d, 1H), 6.64 (s, 1H), 5.17 (s, 2H), 3.56 (s, 3H).

Example 3

(rac)-5-Fluoro-4-(4-fluoro-1-benzofuran-7-yl)-N-{4-[(S-methylsulfonimidoyl)methyl]-6-(trifluoromethyl)pyridin-2-yl}pyridin-2-amine

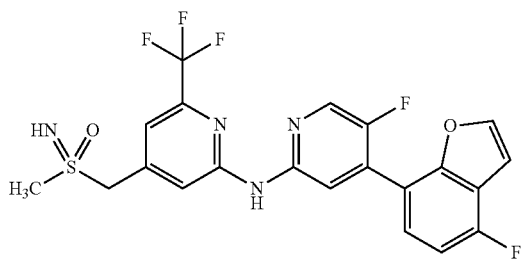 [SMILES: CS(=N)(=O)Cc1cc(Nc2cc(-c3ccc(F)c4ccoc34)c(F)cn2)nc(C(F)(F)F)c1]

Example 4

(rac)-2,2,2-Trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)oxido-λ$^6$-sulfanylidene]acetamide

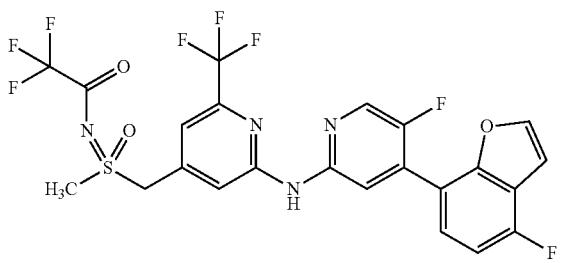 [SMILES: CS(=O)(Cc1cc(Nc2cc(-c3ccc(F)c4ccoc34)c(F)cn2)nc(C(F)(F)F)c1)=NC(=O)C(F)(F)F]

Preparation of Intermediate 3.1

5-Fluoro-4-(4-fluoro-1-benzofuran-7-yl)pyridin-2-amine

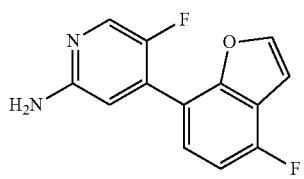 [SMILES: Nc1cc(-c2ccc(F)c3ccoc23)c(F)cn1]

A solution of lithium bis(trimethylsilyl)amide in THF (1M; 2.03 mL; 2.03 mmol; Aldrich Chemical Company Inc.) was added to a mixture of 2-chloro-5-fluoro-4-(4-fluoro-1-benzofuran-7-yl)pyridine (270 mg; 1.02 mmol, prepared as described for intermediate 1.1), tris(dibenzylideneacetone)dipalladium (0) (18.6 mg; 0.02 mmol; Aldrich Chemical Company Inc.) and 2-(dicyclohexylphosphino)-2',4',6'-triisopropylbiphenyl (19.3 mg; 0.04 mmol; Aldrich Chemical Company Inc.) in THF (2 mL) under an atmosphere of argon at room temperature. The mixture was stirred at 60° C. for 6 hours. The mixture was cooled to −20° C. and water (10 ml) was added. The mixture was slowly warmed to room temperature under stirring, solid sodium chloride was added and the mixture was extracted with ethyl acetate (2x). The combined organic phases were filtered using a Whatman filter and concentrated. The residue was purified by chromatography on silica gel (hexanes/ethyl acetate) to yield the title compound (133 mg; 0.47 mmol).

$^1$H-NMR (400 MHz, DMSO-$d_6$): δ [ppm]=8.13 (d, 1H), 8.01 (d, 1H), 7.44 (ddd, 1H), 7.24 (dd, 1H), 7.18 (d, 1H), 6.67 (d, 1H), 5.99 (s, 2H).

Preparation of Intermediate 3.2

2-Chloro-4-[(methylsulfanyl)methyl]-6-(trifluoromethyl)pyridine

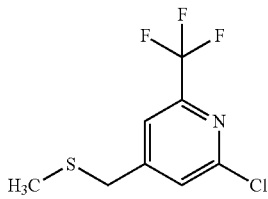

Sodium methanethiolate (254 mg; 3.6 mmol) was added to a stirred solution of 2-chloro-4-(chloromethyl)-6-(trifluoromethyl)pyridine (490 mg; 1.18 mmol; Anichem LLC; CAS #1196154-47-8) in ethanol (15 mL) at 0° C. The cold bath was removed and the batch was stirred at room temperature for 3 hours. The batch was diluted with saturated aqueous sodium chloride solution and extracted with ethyl acetate (2x). The combined organic phases were washed with water, dried (sodium sulfate), filtered and concentrated to give the crude product. Purification by chromatography on silica gel (hexanes/ethyl acetate) yielded the title compound (446 mg; 1.68 mmol).

$^1$H-NMR (400 MHz, DMSO-$d_6$): δ [ppm]=7.91 (s, 1H), 7.82 (s, 1H), 3.84 (s, 2H), 1.97 (s, 3H).

Preparation of Intermediate 3.3

5-Fluoro-4-(4-fluoro-1-benzofuran-7-yl)-N-{4-[(methylsulfanyl)methyl]-6-(trifluoromethyl)pyridin-2-yl}pyridin-2-amine

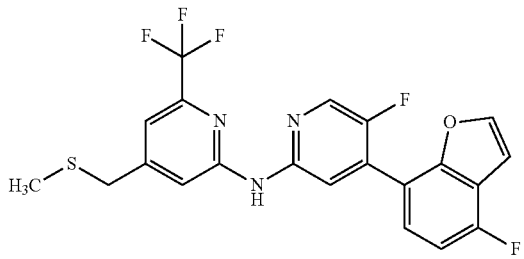 [SMILES: CSCc1cc(Nc2cc(-c3ccc(F)c4ccoc34)c(F)cn2)nc(C(F)(F)F)c1]

A mixture of 2-chloro-4-[(methylsulfanyl)methyl]-6-(trifluoromethyl)pyridine (100 mg; 0.35 mmol, intermediate 3.2), 5-fluoro-4-(4-fluoro-1-benzofuran-7-yl)pyridin-2-amine (125 mg; 0.442 mmol, intermediate 3.1), chloro(2-dicyclohexylphosphino-2',4',6'-tri-iso-propyl-1,1'-biphenyl)[2-(2-aminoethyl)phenyl] palladium(II) methyl-tert-butylether adduct (29 mg; 0.035 mmol; ABCR GmbH & CO. KG) and 2-(dicyclohexylphosphino)-2',4',6'-triisopropylbiphenyl (16.8 mg; 0.035 mmol; Aldrich Chemical Company Inc.) and potassium phosphate (375 mg; 1.76 mmol) in toluene (9.4 ml) and NMP (0.94 mL) was stirred under an atmosphere of argon at 110° C. for 180 minutes. After cooling, the batch was diluted with ethyl acetate and washed with aqueous sodium chloride solution. The organic phase was filtered using a Whatman filter and concentrated. The residue was purified by chromatography on silica gel (hexanes/ethyl acetate) to yield the title compound (140 mg; 0.29 mmol).

$^1$H-NMR (400 MHz, DMSO-$d_6$): δ [ppm]=10.35 (s, 1H), 8.43 (d, 1H), 8.25 (d, 1H), 8.13 (d, 1H), 7.80 (s, 1H), 7.53 (dd, 1H), 7.33-7.27 (m, 2H), 7.21 (d, 1H), 3.78 (s, 2H), 2.02 (s, 3H).

Preparation of Intermediate 3.4

(rac)-2,2,2-Trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)-$\lambda^4$-sulfanylidene]acetamide

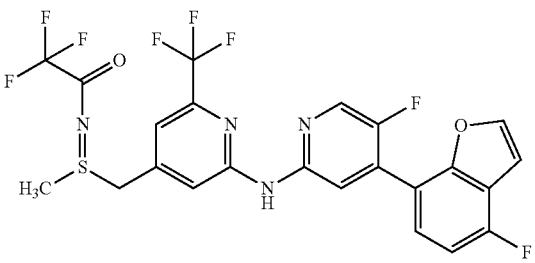 [SMILES: CS(Cc1cc(Nc2cc(-c3ccc(F)c4ccoc34)c(F)cn2)nc(C(F)(F)F)c1)=NC(=O)C(F)(F)F]

Under an atmosphere of argon, a solution of 2,2,2-trifluoroacetamide (61.4 mg; 0.527 mmol) in dioxane (2 mL) was added dropwise to a solution of sodium tert.-butoxide (26.1 mg; 0.26 mmol) in dioxane (2 mL), so that the temperature of the mixture remained below 10° C. Subsequently, a freshly prepared solution of 1,3-dibromo-5,5-dimethylhydantoin (56.5 mg; 0.198 mmol) in dioxane (2 mL) was added dropwise to the stirred mixture, so that the temperature of the mixture remained below 10° C. Then the mixture was stirred for 10 minutes at ambient temperature. Finally, a solution of 5-fluoro-4-(4-fluoro-1-benzofuran-7-yl)-N-{4-[(methylsulfanyl)methyl]-6-(trifluoromethyl)pyridin-2-yl}pyridin-2-amine (128 mg; 0.264 mmol, intermediate 3.3) in dioxane (2 mL) was added dropwise to the stirred mixture. The mixture was stirred for 30 minutes. The batch was diluted with ethyl acetate and an aqueous solution of sodium sulfite (10%) was added. The batch was extracted with ethyl acetate (3x). The combined organic phases were washed with an aqueous solution of sodium chloride, dried over sodium sulfate and concentrated. The residue was purified by chromatography on silica gel (hexanes/ethyl acetate) to yield the title compound (109 mg; 0.18 mmol).

$^1$H-NMR (400 MHz, DMSO-$d_6$): δ [ppm]=10.52 (s, 1H), 8.41 (d, 1H), 8.16 (d, 1H), 8.13 (d, 1H), 7.93 (s, 1H), 7.53 (dd, 1H), 7.31 (dd, 1H), 7.25 (d, 1H), 7.21 (d, 1H), 4.77-4.48 (m, 2H), 2.83 (s, 3H).

Preparation of End Products

To a solution of (rac)-2,2,2-trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)-λ$^4$-sulfanylidene]acetamide (98 mg; 0.162 mmol, intermediate 3.4) in methanol (7 mL) and water (0.2 mL) was added an solution of Oxone® (84.6 mg; 0.137 mmol) in water (0.58 mL). The pH was maintained between 6.8 and 7.2 by addition of aqueous solution of potassium hydroxide (5%), if necessary. The mixture was stirred for 30 min. The reaction mixture was diluted with water and extracted with ethyl acetate (3×). The combined organic phases were washed with an aqueous solution of sodium sulfite (10%), dried over sodium sulfate and concentrated. The residue was purified by chromatography on silica gel (hexanes/ethyl acetate) to yield (rac)-5-fluoro-4-(4-fluoro-1-benzofuran-7-yl)-N-{4-[(S-methylsulfonimidoyl)methyl]-6-(trifluoromethyl)pyridin-2-yl}pyridin-2-amine (40.2 mg; 0.08 mmol; example 3) and (rac)-2,2,2-trifluoro-N-[{2-{[5-fluoro-4-(4-fluoro-1-benzofuran-7-yl)pyridin-2-yl]amino}-6-(trifluoromethyl)pyridin-4-yl]methyl}(methyl)oxido-λ$^6$-sulfanylidene]acetamide (20.3 mg; 0.04 mmol; example 4).

Example 3

$^1$H-NMR (400 MHz, DMSO-d$_6$): δ [ppm]=10.43 (s, 1H), 8.42 (d, 1H), 8.24 (d, 1H), 8.13 (d, 1H), 7.88 (s, 1H), 7.53 (dd, 1H), 7.41 (s, 1H), 7.35-7.27 (m, 1H), 7.21 (d, 1H), 4.53 (s, 2H), 3.91 (s, 1H), 2.92 (s, 3H).

Example 4

$^1$H-NMR (400 MHz, DMSO-d$_6$): δ [ppm]=10.58 (s, 1H), 8.41 (d, 1H), 8.18 (d, 1H), 8.13 (d, 1H), 8.03 (s, 1H), 7.54 (dd, 1H), 7.36 (s, 1H), 7.31 (t, 1H), 7.22 (d, 1H), 5.29-5.20 (m, 2H), 3.60 (s, 3H).

Example 5

(rac)-5-Fluoro-4-(4-fluoro-1-benzofuran-7-yl)-N-{4-[(S-methylsulfonimidoyl)methyl]pyridin-2-yl}pyridin-2-amine

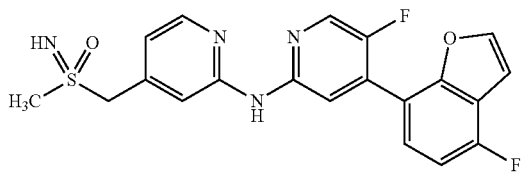 [SMILES: CS(=N)(=O)Cc1ccnc(Nc2cc(-c3ccc(F)c4ccoc34)c(F)cn2)c1]

Example 6

(rac)-2,2,2-Trifluoro-N-{[(2-{[5-fluoro-4-(4-fluoro-1-benzofuran-7-yl)pyridin-2-yl]amino}pyridin-4-yl)methyl](methyl)oxido-λ$^6$-sulfanylidene}acetamide

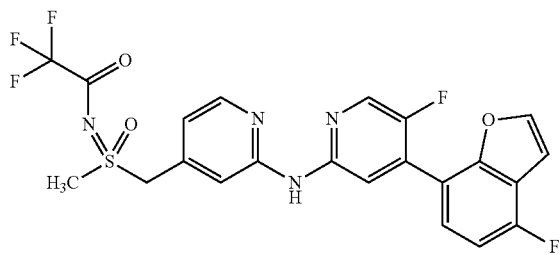 [SMILES: CS(=O)(Cc1ccnc(Nc2cc(-c3ccc(F)c4ccoc34)c(F)cn2)c1)=NC(=O)C(F)(F)F]

Preparation of Intermediate 5.1

5-Fluoro-4-(4-fluoro-1-benzofuran-7-yl)-N-{4-[(methylsulfanyl)methyl]pyridin-2-yl}pyridin-2-amine

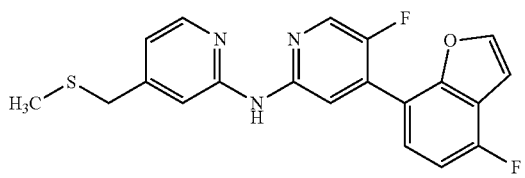 [SMILES: CSCc1ccnc(Nc2cc(-c3ccc(F)c4ccoc34)c(F)cn2)c1]

A mixture of 4-[(methylsulfanyl)methyl]pyridin-2-amine (1.3 g; 8.47 mmol; UkrOrgSynthesis Ltd., CAS #179554-98-4), 2-chloro-5-fluoro-4-(4-fluoro-1-benzofuran-7-yl)pyridine (1.8 g; 6.77 mmol; see Intermediate 1.1), chloro(2-dicyclohexylphosphino-2',4',6'-tri-iso-propyl-1,1'-biphenyl)[2-(2-aminoethyl)phenyl] palladium(II) methyl-tert-butylether adduct (560 mg; 0.678 mmol; ABCR GmbH & Co. KG) and 2-(dicyclohexylphosphino)-2',4',6'-triisopropylbiphenyl (323 mg; 0.678 mmol; Aldrich Chemical Company Inc.) and potassium phosphate (7.19 g; 33.87 mmol) in toluene (180 mL) and NMP (18 mL) was stirred under an atmosphere of argon at 130° C. for 3 hours. After cooling, the batch was diluted with ethyl acetate and washed with aqueous sodium chloride solution. The organic phase was dried over sodium sulfate and concentrated. The residue was purified by chromatography on silica gel (hexane/ethyl acetate) to yield the title compound (2.63 g; 6.52 mmol).

$^1$H-NMR (400 MHz, DMSO-d$_6$): δ [ppm]=9.85 (s, 1H), 8.37 (d, 1H), 8.18-8.08 (m, 3H), 7.56-7.47 (m, 2H), 7.29 (dd, 1H), 7.21 (d, 1H), 6.82 (dd, 1H), 3.65 (s, 2H), 2.01 (s, 3H).

Preparation of Intermediate 5.2

(rac)-2,2,2-Trifluoro-N-[[(2-{[5-fluoro-4-(4-fluoro-1-benzofuran-7-yl)pyridin-2-yl]amino}pyridin-4-yl)methyl](methyl)-λ$^4$-sulfanylidene]acetamide

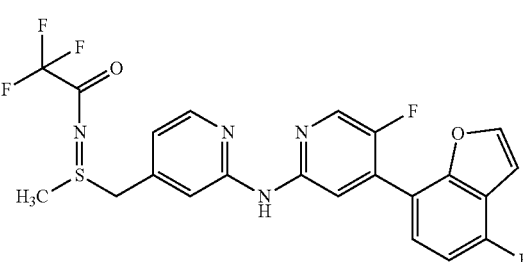

Under an atmosphere of argon, a solution of 2,2,2-trifluoroacetamide (1.513 g; 12.98 mmol) in dioxane (50 mL) was added dropwise to a solution of sodium tert.-butoxide (643.1 mg; 6.49 mmol) in dioxane (50 mL). Subsequently, a freshly prepared solution of 1,3-dibromo-5,5-dimethylhydantoin (1.39 g; 0.5 mmol) in dioxane (50 mL) was added dropwise to the stirred mixture. Then the mixture was stirred for 10 minutes at ambient temperature. Finally, a solution of 5-fluoro-4-(4-fluoro-1-benzofuran-7-yl)-N-{4-[(methylsulfanyl)methyl]pyridin-2-yl}pyridin-2-amine (2.62 g; 6.49 mmol; intermediate 5.1) in dioxane (50 mL) was added dropwise to the stirred mixture. The mixture was stirred for 60 minutes. The batch was diluted with ethyl acetate and an aqueous solution of sodium sulfite (10%) was added. The batch was extracted with ethyl acetate (3×). The combined organic phases were washed with an aqueous solution of sodium chloride, dried over sodium sulfate and concentrated. The residue was purified by chromatography on silica gel (hexanes/ethyl acetate) to yield the title compound (2.2 g; 3.84 mmol).

$^1$H-NMR (400 MHz, DMSO-$d_6$): δ [ppm]=10.01 (s, 1H), 8.35 (d, 1H), 8.21 (d, 1H), 8.16 (d, 1H), 8.05 (d, 1H), 7.66 (s, 1H), 7.52 (dd, 1H), 7.29 (dd, 1H), 7.21 (d, 1H), 6.83 (dd, 1H), 4.62-4.40 (m, 2H), 2.80 (s, 3H).

Preparation of End Products

To a solution of (rac)-2,2,2-trifluoro-N-[[(2-{[5-fluoro-4-(4-fluoro-1-benzofuran-7-yl)pyridin-2-yl]amino}pyridin-4-yl)methyl](methyl)-λ4-sulfanylidene]acetamide (2.01 g; 3.82 mmol, intermediate 5.2) in methanol (280 mL) water (5 mL) was added an solution of Oxone® (contains potassium peroxymonosulfate) (2.93 g; 4.77 mmol) in water (14 mL). The pH was maintained at 7.5 by addition of aqueous solution of potassium hydroxide (5%), if necessary. The mixture was stirred for 25 min. The reaction mixture was diluted with water and extracted with ethyl acetate (3×). The combined organic phases were washed with an aqueous solution of sodium sulfite (10%), dried over sodium sulfate and concentrated. The residue was purified by chromatography on silica gel (hexanes/ethyl acetate/MeOH) to yield (rac)-5-fluoro-4-(4-fluoro-1-benzofuran-7-yl)-N-{4-[(S-methylsulfonimidoyl)methyl]pyridin-2-yl}pyridin-2-amine (121 mg; 0.21 mmol; example 5) and (rac)-2,2,2-trifluoro-N-{[(2-{[5-fluoro-4-(4-fluoro-1-benzofuran-7-yl)pyridin-2-yl]amino}pyridin-4-yl)methyl](methyl)oxido-λ$^6$-sulfanylidene}-acetamide (1.09 g; 2.14 mmol; example 6).

Example 5

$^1$H-NMR (400 MHz, DMSO-$d_6$): δ [ppm]=9.92 (s, 1H), 8.36 (d, 1H), 8.20-8.15 (m, 2H), 8.13 (d, 1H), 7.60 (s, 1H), 7.52 (dd, 1H), 7.33-7.26 (m, 1H), 7.21 (d, 1H), 6.93 (dd, 1H), 4.44-4.32 (m, 2H), 3.75 (s, 1H), 2.89 (s, 3H).

Example 6

$^1$H-NMR (400 MHz, DMSO-$d_6$): δ [ppm]=10.06 (s, 1H), 8.35 (d, 1H), 8.25 (d, 1H), 8.16 (d, 1H), 8.06 (d, 1H), 7.76 (s, 1H), 7.53 (dd, 1H), 7.30 (dd, 1H), 7.21 (d, 1H), 6.93 (dd, 1H), 5.10 (s, 2H), 3.54 (s, 3H).

Alternative Procedure for the Preparation of Example 5

(rac)-5-Fluoro-4-(4-fluoro-1-benzofuran-7-yl)-N-{4-[(S-methylsulfonimidoyl)methyl]pyridin-2-yl}pyridin-2-amine

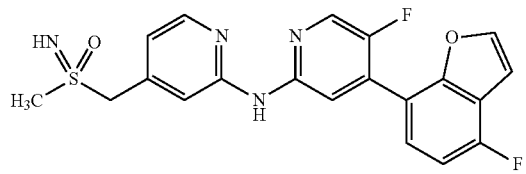 [SMILES: CS(=N)(=O)Cc1ccnc(Nc2cc(-c3ccc(F)c4ccoc34)c(F)cn2)c1]

To a solution of (rac)-2,2,2-trifluoro-N-{[(2-{[5-fluoro-4-(4-fluoro-1-benzofuran-7-yl)pyridin-2-yl]amino}pyridin-4-yl)methyl](methyl)oxido-λ$^6$-sulfanylidene}acetamide (335 mg; 0.657 mmol; Example 6) in methanol (50 mL) potassium carbonate (454 mg; 3.28 mmol) was added. The batch was stirred at ambient temperature for 1 hour. The methanol was removed under reduced pressure and the resulting residue was purified by chromatography on silica gel (hexanes/ethyl acetate/methanol), followed by crystallization from ethanol to give the title compound (179 mg; 0.43 mmol).

$^1$H-NMR (400 MHz, DMSO-$d_6$): δ [ppm]=9.92 (s, 1H), 8.36 (d, 1H), 8.20-8.15 (m, 2H), 8.13 (d, 1H), 7.60 (s, 1H), 7.52 (dd, 1H), 7.29 (dd, 1H), 7.21 (d, 1H), 6.93 (dd, 1H), 4.43-4.33 (m, 2H), 3.75 (s, 1H), 2.89 (s, 3H).

Example 7

(rac)-5-Fluoro-4-(4-fluoro-1-benzofuran-7-yl)-N-{6-methyl-4-[(S-methylsulfonimidoyl)-methyl]pyridin-2-yl}pyridin-2-amine

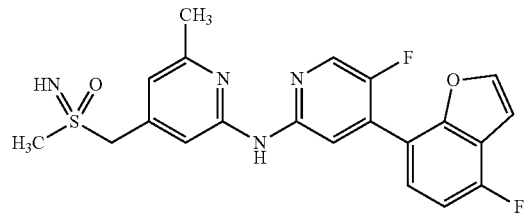 [SMILES: Cc1cc(CS(C)(=N)=O)cc(Nc2cc(-c3ccc(F)c4ccoc34)c(F)cn2)n1]

Preparation of Intermediate 7.1

(2-Chloro-6-methylpyridin-4-yl)methanol

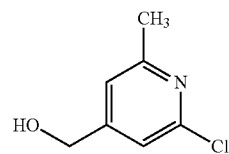

To a stirred solution of 2-chloro-6-methylisonicotinic acid (2 g; 11.1 mmol; ACROS Organics, CAS #25462-85-5) in THF (29 mL) at 0° C. was added a 1M solution of borane-tetrahydrofuran complex in THF (33.2 mL; 33.2 mmol). The mixture was allowed to react at RT overnight. Then, the batch was diluted with EtOAc (350 mL) and aqueous sodium hydroxide solution (1N; 330 mL) was added. After phase separation the organic layer was washed with saturated aqueous sodium chloride solution, dried (sodium sulfate), and concentrated to yield the title compound (1.67 g).

$^1$H-NMR (400 MHz, DMSO-$d_6$): δ [ppm]=7.19 (d, 1H), 5.48 (t, 1H), 4.51 (d, 2H), 2.43 (s, 3H).

Preparation of Intermediate 7.2

(2-Amino-6-methylpyridin-4-yl)methanol

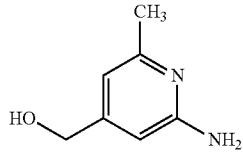

A solution of lithium bis(trimethylsilyl)amide in THF (1M; 12.69 mL; 12.69 mmol; Aldrich Chemical Company Inc.) was added to a mixture of (2-chloro-6-methylpyridin-4-yl)methanol (1 g; 6.34 mmol, intermediate 3.1), tris(dibenzylideneacetone)dipalladium (0) (116.6 mg; 0.127 mmol; Aldrich Chemical Company Inc.) and 2-(dicyclohexylphosphino)-2',4',6'-triisopropylbiphenyl (120.9 mg; 0.254 mmol; Aldrich Chemical Company Inc.) in THF (12.5 mL) under an atmosphere of argon at room temperature. The mixture was stirred at 60° C. for 3 hours. The mixture was cooled to −20° C. and 1 M hydrochloric acid was added until a $p_H$ value between 4 and 6 was reached. The mixture was slowly warmed to room temperature under stirring and aqueous sodium hydroxide solution (5N) was added to adjust a $p_H$ value between 10 and 11. After addition of brine (150 mL) the mixture was extracted with ethyl acetate. The combined organic phases were dried (sodium sulfate), filtered, and concentrated. The residue was purified by chromatography on silica gel (ethyl acetate/methanol) to yield the title compound (600 mg; 4.34 mmol).

$^1$H-NMR (400 MHz, DMSO-$d_6$): δ [ppm]=11.08-11.05 (m, 1H), 6.26 (s, 1H), 6.22 (s, 1H), 5.69 (s, 2H), 5.12 (t, 1H), 4.31 (d, 2H), 2.19 (s, 3H).

Preparation of Intermediate 7.3

4-(Chloromethyl)-6-methylpyridin-2-amine

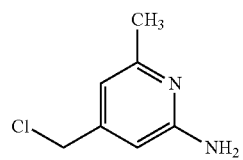

To a stirred solution of (2-amino-6-methylpyridin-4-yl)methanol (306 mg; 2.22 mmol, intermediate 7.2) in DCM (10.8 mL) and NMP (0.72 mL) at 0° C. was added dropwise thionyl chloride (0.4 mL; 5.54 mmol). The mixture was allowed to react at room temperature overnight. The batch was diluted with aqueous sodium bicarbonate solution and aqueous sodium chloride solution and extracted with DCM (3×). The combined organic phases were filtered, dried over sodium sulfate, and concentrated. The crude material was purified by chromatography on silica gel (ethyl acetate/methanol) to yield the desired product (360 mg; 1.77 mmol).

$^1$H-NMR (400 MHz, DMSO-$d_6$): δ [ppm]=6.36 (s, 1H), 6.27 (s, 1H), 5.94 (br. s., 2H), 4.53 (s, 2H), 2.24-2.20 (m, 3H).

Preparation of Intermediate 7.4

6-Methyl-4-[(methylsulfanyl)methyl]pyridin-2-amine

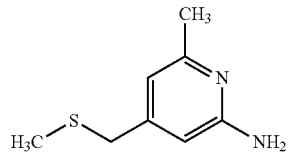

Intermediate 7.4 was prepared under similar conditions as described in the preparation of Intermediate 1.5 using 4-(chloromethyl)-6-methylpyridin-2-amine (Intermediate 7.3).

$^1$H-NMR (300 MHz, DMSO-$d_6$): δ [ppm]=6.28 (s, 1H), 6.16 (s, 1H), 5.79 (s, 2H), 3.46 (s, 2H), 2.19 (s, 3H), 1.95 (s, 3H).

Preparation of Intermediate 7.5

5-Fluoro-4-(4-fluoro-1-benzofuran-7-yl)-N-{6-methyl-4-[(methylsulfanyl)methyl]pyridin-2-yl}pyridin-2-amine

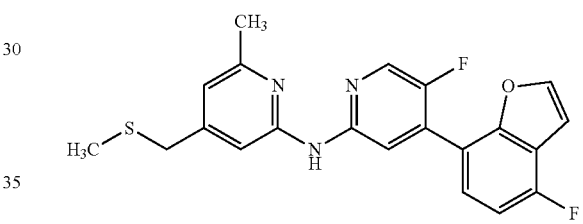

Intermediate 7.5 was prepared under similar conditions as described in the preparation of Intermediate 1.6 using 6-methyl-4-[(methylsulfanyl)methyl]pyridin-2-amine (Intermediate 7.4) and 2-chloro-5-fluoro-4-(4-fluoro-1-benzofuran-7-yl)pyridine (Intermediate 1.1).

$^1$H-NMR (400 MHz, DMSO-$d_6$): δ [ppm]=9.79 (s, 1H), 8.35 (d, 1H), 8.21 (d, 1H), 8.17 (d, 1H), 7.53 (dd, 1H), 7.42 (s, 1H), 7.33-7.25 (m, 1H), 7.21 (d, 1H), 6.70 (s, 1H), 3.61 (s, 2H), 2.34 (s, 3H), 2.00 (s, 3H).

Preparation of Intermediate 7.6

(rac)-2,2,2-Trifluoro-N-[[(2-{[5-fluoro-4-(4-fluoro-1-benzofuran-7-yl)pyridin-2-yl]amino}-6-methyl-pyridin-4-yl)methyl](methyl)λ$^4$-sulfanylidene]acetamide

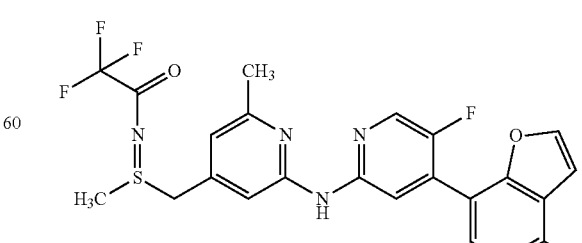

Intermediate 7.6 was prepared under similar conditions as described in the preparation of Intermediate 1.7 using 5-fluoro-4-(4-fluoro-1-benzofuran-7-yl)-N-{6-methyl-4-[(methylsulfanyl)methyl]pyridin-2-yl}pyridin-2-amine (Intermediate 7.5).

$^1$H-NMR (400 MHz, DMSO-d$_6$): δ [ppm]=9.96 (s, 1H), 8.33 (d, 1H), 8.17 (d, 1H), 8.11 (d, 1H), 7.57-7.50 (m, 2H), 7.33-7.26 (m, 1H), 7.21 (d, 1H), 6.69 (s, 1H), 4.54 (d, 1H), 4.39 (d, 1H), 2.79 (s, 3H), 2.35 (s, 3H).

Preparation of End Product

Example 7 was prepared under similar conditions as described in the preparation of Example 1 using (rac)-2,2,2-trifluoro-N-[[(2-{[5-fluoro-4-(4-fluoro-1-benzofuran-7-yl)pyridin-2-yl]amino}-6-methylpyridin-4-yl)methyl](methyl)-λ$^4$-sulfanylidene]acetamide (Intermediate 7.6).

$^1$H-NMR (400 MHz, DMSO-d$_6$): δ [ppm]=9.86 (s, 1H), 8.34 (d, 1H), 8.20 (d, 1H), 8.17 (d, 1H), 7.54 (dd, 1H), 7.48 (s, 1H), 7.29 (dd, 1H), 7.21 (d, 1H), 6.80 (s, 1H), 4.39-4.27 (m, 2H), 3.72 (s, 1H), 2.89 (s, 3H), 2.36 (s, 3H).

Example 8

(rac)-N-{6-Ethyl-4-[(S-methylsulfonimidoyl)methyl]pyridin-2-yl}-5-fluoro-4-(4-fluoro-1-benzofuran-7-yl)pyridin-2-amine

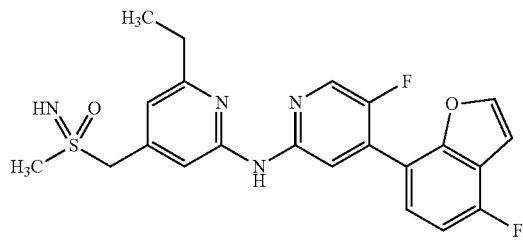 [SMILES: CCc1cc(CS(C)(=N)=O)cc(Nc2cc(-c3ccc(F)c4ccoc34)c(F)cn2)n1]

Preparation of Intermediate 8.1

2-Chloro-6-ethylpyridine-4-carboxylic acid

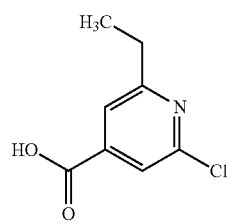

Phosphorus oxychloride (19.8 mL; 213.1 mmol) was added to 6-ethyl-2-oxo-1,2-dihydropyridine-4-carboxylic acid (2.5 g; 14.2 mmol; Manchester Organics Ltd.; CAS #54881-17-3). The mixture was heated at 100° C. for 30 minutes. Then, the batch was evaporated under reduced pressure and the resulting residue was added to ice-water. The mixture was extracted with DCM and ethyl acetate. The combined organic phases were dried (sodium sulfate), filtered, and concentrated to yield the title compound as a brown solid (2.6 g; 13.31 mmol).

$^1$H-NMR (400 MHz, DMSO-d$_6$): δ [ppm]=13.89 (br. s., 1H), 7.69 (d, 1H), 7.64 (d, 1H), 2.82 (q, 2H), 1.23 (t, 3H).

Preparation of Intermediate 8.2

(2-Chloro-6-ethylpyridin-4-yl)methanol

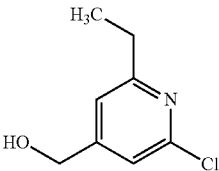

Intermediate 8.2 was prepared under similar conditions as described in the preparation of Intermediate 7.1 using 2-chloro-6-ethylpyridine-4-carboxylic acid (Intermediate 8.1).

$^1$H-NMR (400 MHz, DMSO-d$_6$): δ [ppm]=7.19 (d, 1H), 5.48 (t, 1H), 4.51 (d, 2H), 2.43 (s, 3H).

Preparation of Intermediate 8.3

(2-Amino-6-ethylpyridin-4-yl)methanol

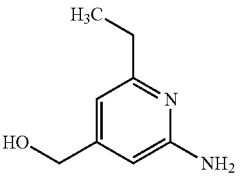

Intermediate 8.3 was prepared under similar conditions as described in the preparation of Intermediate 7.2 using (2-chloro-6-ethylpyridin-4-yl)methanol (Intermediate 8.2).

$^1$H-NMR (400 MHz, DMSO-d$_6$): δ [ppm]=6.27 (s, 1H), 6.23 (s, 1H), 5.69 (s, 2H), 5.12 (t, 1H), 4.32 (d, 2H), 2.48-2.43 (m, 2H), 1.14 (t, 3H).

Preparation of Intermediate 8.4

4-(Chloromethyl)-6-ethylpyridin-2-amine

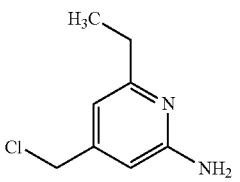

Intermediate 8.4 was prepared under similar conditions as described in the preparation of Intermediate 7.3 using (2-amino-6-ethylpyridin-4-yl)methanol (Intermediate 8.3).

$^1$H-NMR (400 MHz, DMSO-d$_6$): δ [ppm]=6.37 (d, 1H), 6.29 (s, 1H), 5.92 (s, 2H), 4.55 (s, 2H), 1.15 (t, 3H).

Preparation of Intermediate 8.5

6-Ethyl-4-[(methylsulfanyl)methyl]pyridin-2-amine

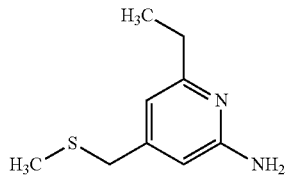

Intermediate 8.5 was prepared under similar conditions as described in the preparation of Intermediate 1.5 using 4-(chloromethyl)-6-ethylpyridin-2-amine (Intermediate 8.4).

$^1$H-NMR (400 MHz, DMSO-d$_6$): δ [ppm]=6.29 (d, 1H), 6.18 (s, 1H), 5.76 (s, 2H), 3.47 (s, 2H), 2.49-2.43 (m, 2H), 1.96 (s, 3H), 1.14 (t, 3H).

Preparation of Intermediate 8.6

N-{6-Ethyl-4-[(methylsulfanyl)methyl]pyridin-2-yl}-5-fluoro-4-(4-fluoro-1-benzofuran-7-yl)pyridin-2-amine

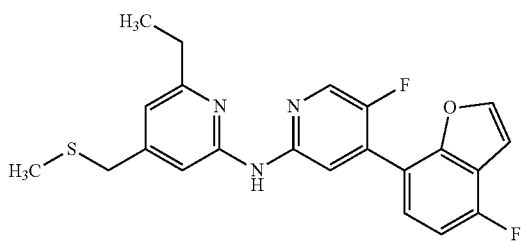 [SMILES: CCc1cc(CSC)cc(Nc2cc(-c3ccc(F)c4ccoc34)c(F)cn2)n1]

Intermediate 8.6 was prepared under similar conditions as described in the preparation of Intermediate 1.6 using 6-ethyl-4-[(methylsulfanyl)methyl]pyridin-2-amine (Intermediate 8.5) and 2-chloro-5-fluoro-4-(4-fluoro-1-benzofuran-7-yl)pyridine (Intermediate 1.1).

$^1$H-NMR (400 MHz, DMSO-d$_6$): δ [ppm]=9.79 (s, 1H), 8.42 (d, 1H), 8.36 (d, 1H), 8.15 (d, 1H), 7.53 (dd, 1H), 7.33-7.25 (m, 2H), 7.21 (d, 1H), 6.69 (s, 1H), 3.62 (s, 2H), 2.61 (q, 2H), 2.01 (s, 3H), 1.14 (t, 3H).

Preparation of Intermediate 8.7

(rac)-N-[[(2-Ethyl-6-{[5-fluoro-4-(4-fluoro-1-benzofuran-7-yl)pyridin-2-yl]amino}pyridin-4-yl)methyl](methyl)-λ$^4$-sulfanylidene]-2,2,2-trifluoroacetamide

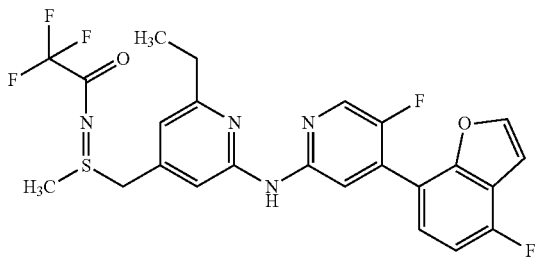 [SMILES: CCc1cc(CS(C)=NC(=O)C(F)(F)F)cc(Nc2cc(-c3ccc(F)c4ccoc34)c(F)cn2)n1]

Intermediate 8.7 was prepared under similar conditions as described in the preparation of Intermediate 1.7 using N-{6-ethyl-4-[(methylsulfanyl)methyl]pyridin-2-yl}-5-fluoro-4-(4-fluoro-1-benzofuran-7-yl)pyridin-2-amine (Intermediate 8.6).

$^1$H-NMR (400 MHz, DMSO-d$_6$): δ [ppm]=9.96 (s, 1H), 8.35 (d, 1H), 8.30 (d, 1H), 8.15 (d, 1H), 7.53 (dd, 1H), 7.42 (s, 1H), 7.29 (dd, 1H), 7.21 (d, 1H), 6.68 (s, 1H), 4.58-4.36 (m, 2H), 2.79 (s, 3H), 2.62 (q, 2H), 1.15 (t, 3H).

Preparation of End Product

Example 8 was prepared under similar conditions as described in the preparation of Example 1 using (rac)-N-[[(2-ethyl-6-{[5-fluoro-4-(4-fluoro-1-benzofuran-7-yl)pyridin-2-yl]amino}pyridin-4-yl)methyl](methyl)-λ$^4$-sulfanylidene]-2,2,2-trifluoroacetamide (Intermediate 8.7).

$^1$H-NMR (400 MHz, DMSO-d$_6$): δ [ppm]=9.86 (s, 1H), 8.40 (d, 1H), 8.35 (d, 1H), 8.15 (d, 1H), 7.53 (dd, 1H), 7.37 (s, 1H), 7.29 (dd, 1H), 7.21 (d, 1H), 6.79 (s, 1H), 4.39-4.27 (m, 2H), 3.72 (s, 1H), 2.89 (s, 3H), 2.63 (q, 2H), 1.15 (t, 3H).

Example 9

(rac)-{[(2-{[5-fluoro-4-(4-fluoro-1-benzofuran-7-yl)pyridin-2-yl]amino}pyridin-4-yl)methyl]-methyl)oxido-λ$^6$P-sulfanylidene}cyanamide

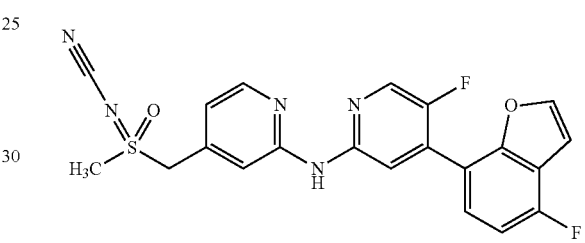

(rac)-5-Fluoro-4-(4-fluoro-1-benzofuran-7-yl)-N-{4-[(S-methylsulfonimidoyl)methyl]pyridin-2-yl}pyridin-2-amine (60 mg; 0.145 mmol; Example 5) was dissolved in DCM (4 mL). To this solution cyanogen bromide (3M solution in DCM; 72.4 µl; 0.217 mmol) and N,N-dimethylpyridin-4-amine (19.4 mg; 0.159 mmol) were added. The batch was allowed to react at room temperature for 4.5 hours. Then, the batch was evaporated under reduced pressure and the resulting residue was purified by preparative HPLC to yield the title compound (27.6 mg; 0.03 mmol).

$^1$H-NMR (400 MHz, DMSO-d$_6$): δ [ppm]=10.07 (s, 1H), 8.37 (s, 1H), 8.26 (d, 1H), 8.16 (d, 1H), 8.09 (d, 1H), 7.74 (s, 1H), 7.53 (dd, 1H), 7.30 (t, 1H), 7.21 (d, 1H), 6.96 (d, 1H), 5.10-5.00 (m, 2H), 3.46 (s, 3H).

Example 10

(rac)-N-{[(2-{[5-fluoro-4-(4-fluoro-1-benzofuran-7-yl)pyridin-2-yl]amino}pyridin-4-yl)methyl](methyl)oxido-λ$^6$-sulfanylidene}acetamide

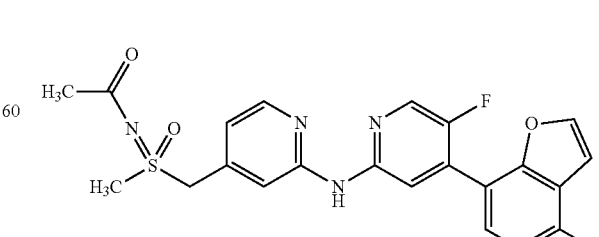

Acetyl chloride (16.1 mg; 0.20 mmol) was added to a stirred solution of (rac)-5-fluoro-4-(4-fluoro-1-benzofuran-7-yl)-N-{4-[(S-methylsulfonimidoyl)-methyl]-pyridin-2-yl}pyridin-2-amine (90 mg; 0.185 mmol; Example 5) and triethylamine (46.7 mg; 0.46 mmol) in DCM (4 mL) at 0° C. The ice bath was removed and the mixture was stirred for 2 hours at RT before it was diluted with water and extracted twice with ethyl acetate. The combined organic layers were filtered using a Whatman filter and concentrated. The residue was purified by preparative HPLC to yield the title product (39.8 mg; 0.09 mmol).

$^1$H-NMR (400 MHz, DMSO-$d_6$): δ [ppm]=10.02 (s, 1H), 8.36 (d, 1H), 8.22 (d, 1H), 8.16 (d, 1H), 8.08 (d, 1H), 7.69 (s, 1H), 7.52 (dd, 1H), 7.29 (dd, 1H), 7.21 (d, 1H), 6.92 (dd, 1H), 4.91-4.82 (m, 2H), 3.23 (s, 3H), 1.95 (s, 3H).

Example 11

(rac)-Ethyl {[2-{[5-fluoro-4-(4-fluoro-1-benzofuran-7-yl)pyridin-2-yl]amino}pyridin-4-yl)methyl]-(methyl)oxido-λ$^6$-sulfanylidene}carbamate

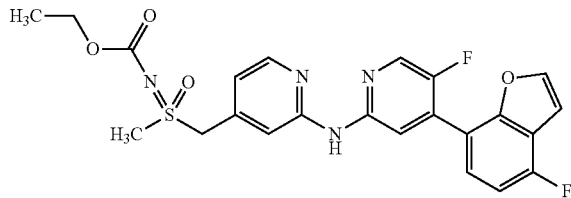 [SMILES: CCOC(=O)N=S(C)(=O)Cc1ccnc(Nc2cc(-c3ccc(F)c4ccoc34)c(F)cn2)c1]

Ethyl chloroformate (26.8 mg; 0.24 mmol) was added dropwise to a stirred solution of (rac)-5-fluoro-4-(4-fluoro-1-benzofuran-7-yl)-N-{4-[(S-methylsulfonimidoyl)-methyl]-pyridin-2-yl}pyridin-2-amine (90 mg; 0.185 mmol; Example 5) in pyridine (3 mL) at 0° C. The ice bath was removed and the mixture was stirred for 2 hours at RT before it was concentrated under reduced pressure. The residue was dissolved in ethyl acetate and washed with an aqueous solution of sodium chloride. The organic layer was filtered using a Whatman filter and concentrated. The residue was purified by preparative HPLC to yield the title compound (60.9 mg; 0.13 mmol).

$^1$H-NMR (400 MHz, DMSO-$d_6$): δ [ppm]=10.02 (s, 1H), 8.36 (d, 1H), 8.23 (d, 1H), 8.16 (d, 1H), 8.08 (d, 1H), 7.69 (s, 1H), 7.53 (dd, 1H), 7.29 (dd, 1H), 7.21 (d, 1H), 6.93 (dd, 1H), 4.92-4.83 (m, 2H), 3.99 (q, 2H), 3.27 (s, 3H), 1.15 (t, 3H).

Example 12

(rac)-1-Ethyl-3-{[(2-{[5-fluoro-4-(4-fluoro-1-benzofuran-7-yl)pyridin-2-yl]amino}pyridin-4-yl)methyl](methyl)oxido-λ$^6$-sulfanylidene}urea

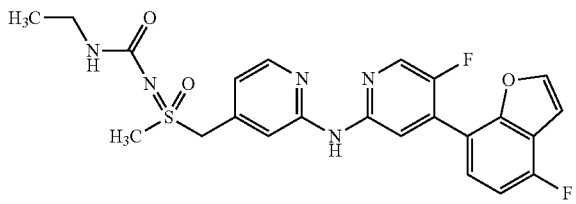 [SMILES: CCNC(=O)N=S(C)(=O)Cc1ccnc(Nc2cc(-c3ccc(F)c4ccoc34)c(F)cn2)c1]

Ethyl isocyanate (13.4 mg; 0.19 mmol) was added to a stirred solution of (rac)-5-fluoro-4-(4-fluoro-1-benzofuran-7-yl)-N-{4-[(S-methylsulfonimidoyl)-methyl]-pyridin-2-yl}pyridin-2-amine (90 mg; 0.185 mmol; Example 5) and triethylamine (19 mg; 0.19 mmol) in DMF (3 mL) at RT. The mixture was stirred for 20 hours at RT before it was diluted with an aqueous solution of sodium chloride and extracted twice with ethyl acetate. The combined organic layers were filtered using a Whatman filter and concentrated. The residue was purified by preparative HPLC to yield the title product (49.3 mg; 0.10 mmol).

$^1$H-NMR (400 MHz, DMSO-$d_6$): δ [ppm]=9.95 (s, 1H), 8.36 (d, 1H), 8.20 (d, 1H), 8.16 (d, 1H), 8.07 (d, 1H), 7.69 (s, 1H), 7.52 (dd, 1H), 7.29 (dd, 1H), 7.21 (d, 1H), 6.94 (dd, 1H), 6.78 (t, 1H), 4.84 (s, 2H), 3.12 (s, 3H), 3.03-2.94 (m, 2H), 0.97 (t, 3H).

Example 13

(rac)-1-{[(2-{[5-Fluoro-4-(4-fluoro-1-benzofuran-7-yl)pyridin-2-yl]amino}pyridin-4-yl)methyl](methyl)oxido-λ$^6$-sulfanylidene}-3-(2,2,2-trifluoroethyl)urea

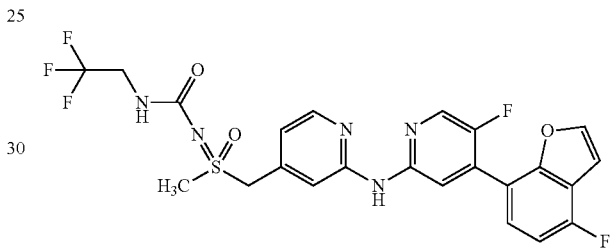

2,2,2-Trifluoroethylisocyanate (23.1 mg; 0.19 mmol) was added to a stirred solution of (rac)-5-fluoro-4-(4-fluoro-1-benzofuran-7-yl)-N-{4-[(S-methylsulfonimidoyl)-methyl]-pyridin-2-yl}pyridin-2-amine (90 mg; 0.185 mmol; Example 5) and triethylamine (19 mg; 0.19 mmol) in DMF (3 mL) at RT. The mixture was stirred for 20 hours at RT before it was diluted with an aqueous solution of sodium chloride and extracted twice with ethyl acetate. The combined organic layers were filtered using a Whatman filter and concentrated. The residue was purified by preparative HPLC to yield the title product (42.2 mg; 0.08 mmol).

$^1$H-NMR (400 MHz, DMSO-$d_6$): δ [ppm]=9.95 (s, 1H), 8.37 (d, 1H), 8.20 (d, 1H), 8.16 (d, 1H), 8.09 (d, 1H), 7.68 (s, 1H), 7.56-7.46 (m, 2H), 7.33-7.26 (m, 1H), 7.21 (d, 1H), 6.94 (d, 1H), 4.87 (s, 2H), 3.82-3.68 (m, 2H), 3.19 (s, 3H).

Examples 14 and 15

Enantiomers of 5-Fluoro-4-(4-fluoro-1-benzofuran-7-yl)-N-{4-[(S-methylsulfonimidoyl)-methyl]pyridin-2-yl}pyridin-2-amine

1 g of racemic (5-fluoro-4-(4-fluoro-1-benzofuran-7-yl)-N-{4-[(S-methylsulfonimidoyl)methyl]-pyridin-2-yl}pyridin-2-amine (Example 5) was separated into its enantiomers by preparative chiral HPLC:

| | |
|---|---|
| System: | Agilent: Prep 1200, 2xPrep Pump, DLA, MWD, Prep FC |
| Column: | Chiralpak IA 5 µm 250 × 30 mm |
| Solvent: | acetonitrile/ethanol/diethylamine 90:10:0.1 (v/v/v) |
| Flow: | 50 mL/min |
| Temperature: | RT |
| Solution: | 1005 mg/20 mL DCM/MeOH 1:1 |
| Injection: | 40 × 0.5 mL |
| Detection: | UV 280 nm |

| Fractions | Retention time in min | purity in % | yield | Specific optical rotation |
|---|---|---|---|---|
| Example 14 Enantiomer 1 | 7.8-9.6 min | >99.9% | 275 mg | $[\alpha]_D^{20} = +10.9°$ (c = 1.0 g/mL, DMSO) |
| Example 15 Enantiomer 2 | 9.8-12.3. min | 97.6% | 245 mg | $[\alpha]_D^{20} = -10.6°$ (c = 1.0 g/mL, DMSO) |

The following Table 1 provides an overview on the compounds described in the example section:

TABLE 1

| Example No. | Structure | Name of compound |
|---|---|---|
| 1 | 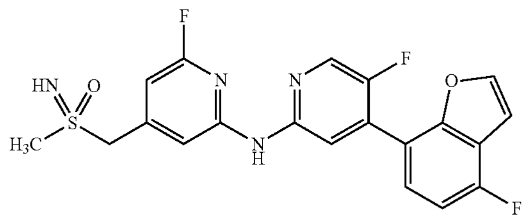 [SMILES: CS(=N)(=O)Cc1cc(F)nc(Nc2cc(-c3ccc(F)c4ccoc34)c(F)cn2)c1] | (rac)-5-Fluoro-4-(4-fluoro-1-benzofuran-7-yl)-N-{6-fluoro-4-[(S-methylsulfonimidoyl)methyl]pyridin-2-yl}pyridin-2-amine |
| 2 | 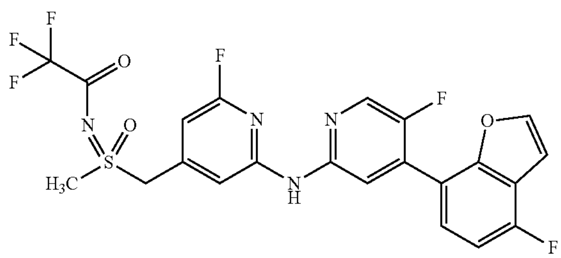 [SMILES: CS(=O)(Cc1cc(F)nc(Nc2cc(-c3ccc(F)c4ccoc34)c(F)cn2)c1)=NC(=O)C(F)(F)F] | (rac)-2,2,2-Trifluoro-N-{[(2-fluoro-6-{[5-fluoro-4-(4-fluoro-1-benzofuran-7-yl)pyridin-2-yl]amino}pyridin-4-yl)methyl](methyl)oxido-$\lambda^6$-sulfanylidene}acetamide |
| 3 | 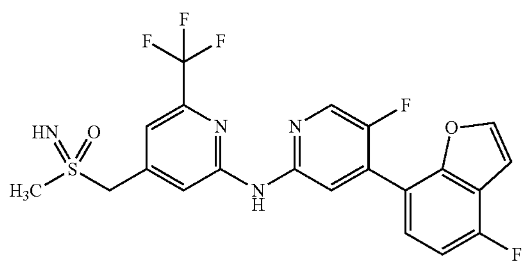 [SMILES: CS(=N)(=O)Cc1cc(Nc2cc(-c3ccc(F)c4ccoc34)c(F)cn2)nc(C(F)(F)F)c1] | (rac)-5-Fluoro-4-(4-fluoro-1-benzofuran-7-yl)-N-{4-[(S-methylsulfonimidoyl)methyl]-6-(trifluoromethyl)pyridin-2-yl}pyridin-2-amine |
| 4 | 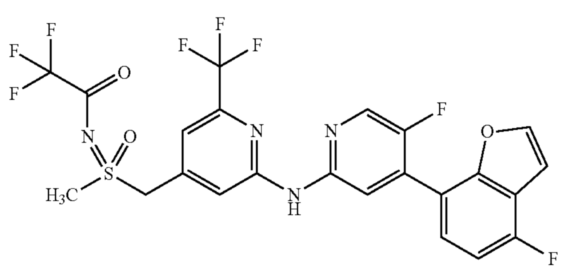 [SMILES: CS(=O)(Cc1cc(Nc2cc(-c3ccc(F)c4ccoc34)c(F)cn2)nc(C(F)(F)F)c1)=NC(=O)C(F)(F)F] | (rac)-2,2,2-Trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)oxido-$\lambda^6$-sulfanylidene]acetamide |
| 5 | 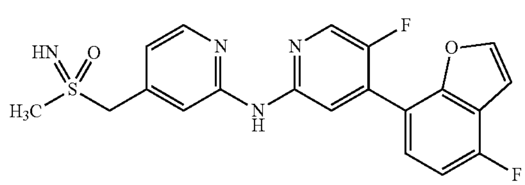 [SMILES: CS(=N)(=O)Cc1ccnc(Nc2cc(-c3ccc(F)c4ccoc34)c(F)cn2)c1] | (rac)-5-Fluoro-4-(4-fluoro-1-benzofuran-7-yl)-N-{4-[(S-methylsulfonimidoyl)methyl]pyridin-2-yl}pyridin-2-amine |

TABLE 1-continued

| Example No. | Structure | Name of compound |
|---|---|---|
| 6 | 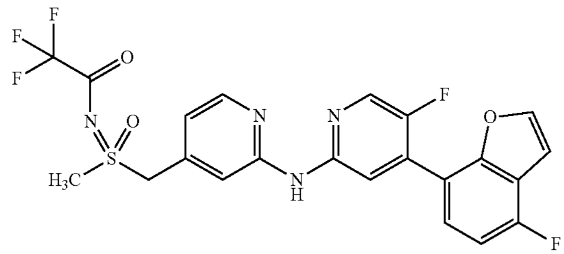 [SMILES: CS(=O)(Cc1ccnc(Nc2cc(-c3ccc(F)c4ccoc34)c(F)cn2)c1)=NC(=O)C(F)(F)F] | (rac)-2,2,2-Trifluoro-N-{[(2-{[5-fluoro-4-(4-fluoro-1-benzofuran-7-yl)pyridin-2-yl]amino}pyridin-4-yl)methyl](methyl)oxido-$\lambda^6$-sulfanylidene}acetamide |
| 7 | 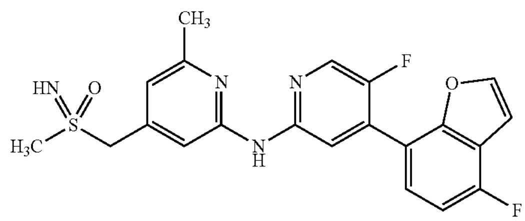 [SMILES: Cc1cc(CS(C)(=N)=O)cc(Nc2cc(-c3ccc(F)c4ccoc34)c(F)cn2)n1] | (rac)-5-Fluoro-4-(4-fluoro-1-benzofuran-7-yl)-N-{6-methyl-4-[(S-methylsulfonimidoyl)methyl]pyridin-2-yl}pyridin-2-amine |
| 8 | 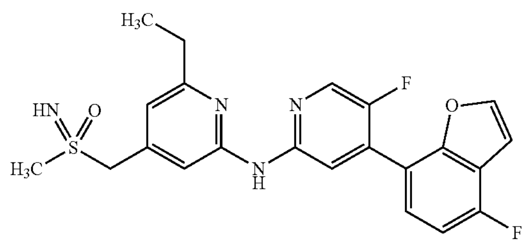 [SMILES: CCc1cc(CS(C)(=N)=O)cc(Nc2cc(-c3ccc(F)c4ccoc34)c(F)cn2)n1] | (rac)-N-{6-Ethyl-4-[(S-methylsulfonimidoyl)methyl]pyridin-2-yl}-5-fluoro-4-(4-fluoro-1-benzofuran-7-yl)pyridin-2-amine |
| 9 | 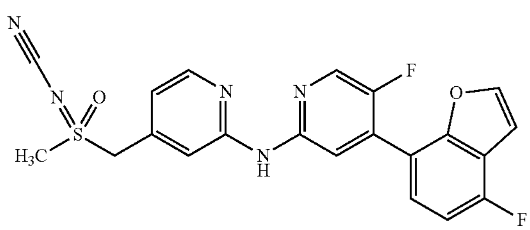 [SMILES: CS(=O)(Cc1ccnc(Nc2cc(-c3ccc(F)c4ccoc34)c(F)cn2)c1)=NC#N] | (rac)-{[(2-{[5-fluoro-4-(4-fluoro-1-benzofuran-7-yl)pyridin-2-yl]amino}pyridin-4-yl)methyl](methyl)oxido-$\lambda^6$-sulfanylidene}cyanamide |
| 10 | 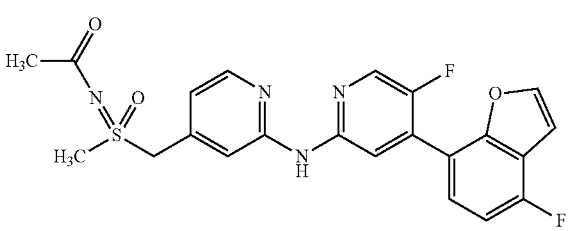 [SMILES: CC(=O)N=S(C)(=O)Cc1ccnc(Nc2cc(-c3ccc(F)c4ccoc34)c(F)cn2)c1] | (rac)-N-{[(2-{[5-fluoro-4-(4-fluoro-1-benzofuran-7-yl)pyridin-2-yl]amino}pyridin-4-yl)methyl](methyl)oxido-$\lambda^6$-sulfanylidene}acetamide |
| 11 | 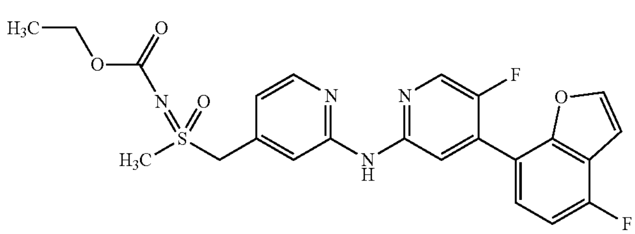 [SMILES: CCOC(=O)N=S(C)(=O)Cc1ccnc(Nc2cc(-c3ccc(F)c4ccoc34)c(F)cn2)c1] | (rac)-Ethyl {[(2-{[5-fluoro-4-(4-fluoro-1-benzofuran-7-yl)pyridin-2-yl]amino}pyridin-4-yl)methyl](methyl)oxido-$\lambda^6$-sulfanylidene}carbamate |

TABLE 1-continued

| Example No. | Structure | Name of compound |
|---|---|---|
| 12 | 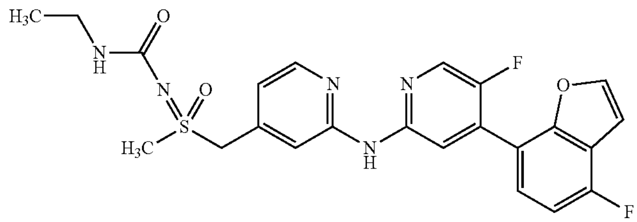 [SMILES: CCNC(=O)N=S(C)(=O)Cc1ccnc(Nc2cc(-c3ccc(F)c4ccoc34)c(F)cn2)c1] | (rac)-1-Ethyl-3-{[(2-{[5-fluoro-4-(4-fluoro-1-benzofuran-7-yl)pyridin-2-yl]amino}pyridin-4-yl)methyl](methyl)oxido-$\lambda^6$-sulfanylidene}urea |
| 13 | 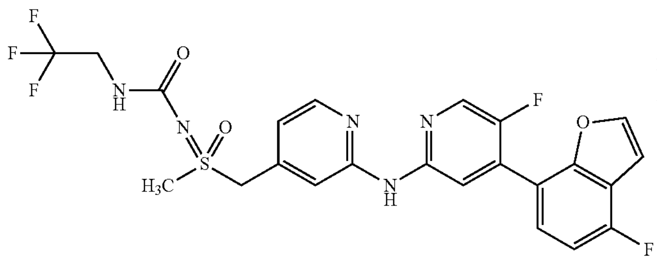 [SMILES: CS(=O)(Cc1ccnc(Nc2cc(-c3ccc(F)c4ccoc34)c(F)cn2)c1)=NC(=O)NCC(F)(F)F] | (rac)-1-{[(2-{[5-Fluoro-4-(4-fluoro-1-benzofuran-7-yl)pyridin-2-yl]amino}pyridin-4-yl)methyl](methyl)oxido-$\lambda^6$-sulfanylidene}-3-(2,2,2-trifluoroethyl)urea |
| 14 | 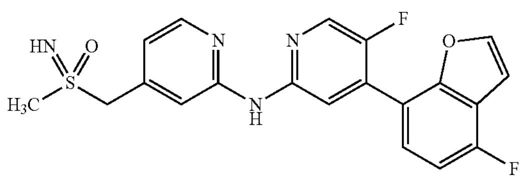 [SMILES: CS(=N)(=O)Cc1ccnc(Nc2cc(-c3ccc(F)c4ccoc34)c(F)cn2)c1] | (+)-5-Fluoro-4-(4-fluoro-1-benzofuran-7-yl)-N-{4-[(S-methylsulfonimidoyl)methyl]pyridin-2-yl}pyridin-2-amine |
| 15 | 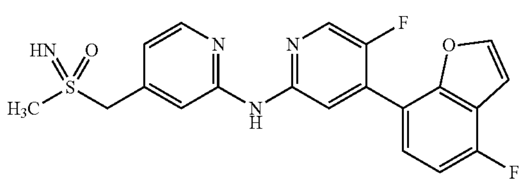 [SMILES: CS(=N)(=O)Cc1ccnc(Nc2cc(-c3ccc(F)c4ccoc34)c(F)cn2)c1] | (−)-5-Fluoro-4-(4-fluoro-1-benzofuran-7-yl)-N-{4-[(S-methylsulfonimidoyl)methyl]pyridin-2-yl}pyridin-2-amine |

Results:

Table 2: Inhibition for CDK9 and CDK2 of compounds according to the present invention The $IC_{50}$ (inhibitory concentration at 50% of maximal effect) values are indicated in nM, "n.t." means that the compounds have not been tested in this assay.

①: Example Number
②: $IC_{50}$ (CDK9): CDK9/CycT1 kinase assay as described under Method 1a. of Materials and Methods
③: $IC_{50}$ (CDK2): CDK2/CycE kinase assay as described under Method 2. of Materials and Methods
④: Selectivity CDK9 over CDK2: $IC_{50}$ (CDK2)/$IC_{50}$ (CDK9) according to Methods 1a. and 2a. of Materials and Methods
⑤: $IC_{50}$ (high ATP CDK9): CDK9/CycT1 kinase assay as described under Method 1b. of Materials and Methods

TABLE 2

| ① | Structure | ② | ③ | ④ | ⑤ |
|---|---|---|---|---|---|
| 1 | 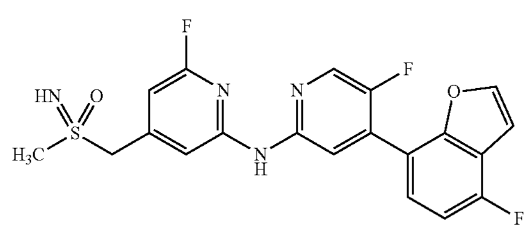 [SMILES: CS(=N)(=O)Cc1cc(F)nc(Nc2cc(-c3ccc(F)c4ccoc34)c(F)cn2)c1] | 4 | 42 | 11 | 1.5 |

TABLE 2-continued
| ① | Structure | ② | ③ | ④ | ⑤ |
|---|---|---|---|---|---|
| 2 | 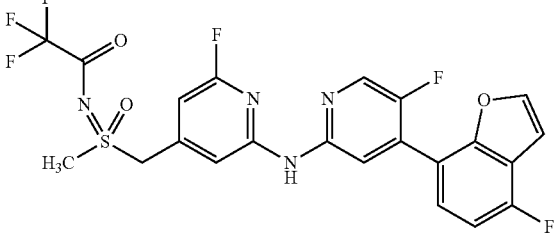 | 7 | 380 | 54 | 7.8 |
| 3 | 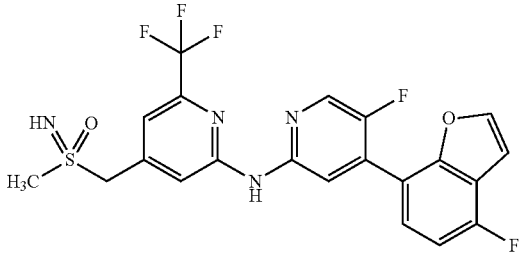 [SMILES: CS(=N)(=O)Cc1cc(Nc2cc(-c3ccc(F)c4ccoc34)c(F)cn2)nc(C(F)(F)F)c1] | 5.8 | 21 | 3.6 | 2.7 |
| 4 | 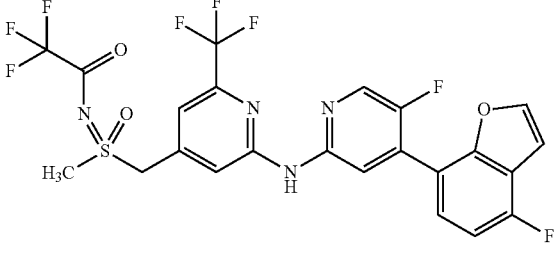 | 19 | 110 | 5.8 | 7 |
| 5 | 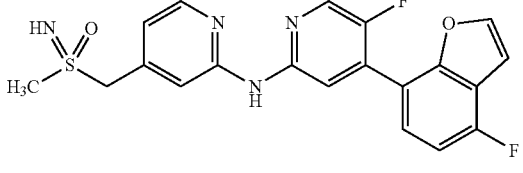 | 3.4 | 130 | 38 | 2 |
| 6 | 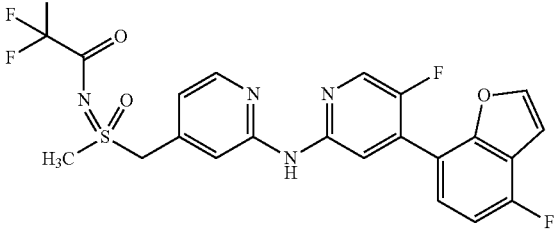 | 4.9 | 540 | 110 | 6.4 |
| 7 | 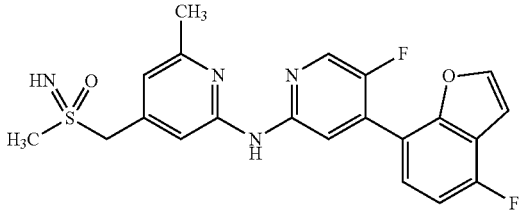 [SMILES: Cc1cc(CS(C)(=N)=O)cc(Nc2cc(-c3ccc(F)c4ccoc34)c(F)cn2)n1] | 2.1 | 39 | 19 | 1.3 |

TABLE 2-continued

| ① | Structure | ② | ③ | ④ | ⑤ |
|---|---|---|---|---|---|
| 8 | 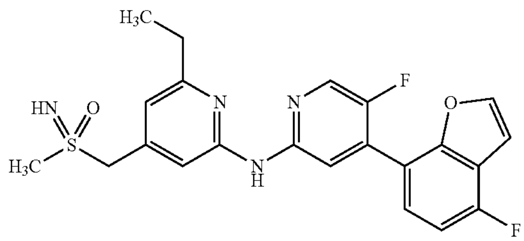 [SMILES: CCc1cc(CS(C)(=N)=O)cc(Nc2cc(-c3ccc(F)c4ccoc34)c(F)cn2)n1] | n.t | 14 | n.t. | 1.3 |
| 9 | 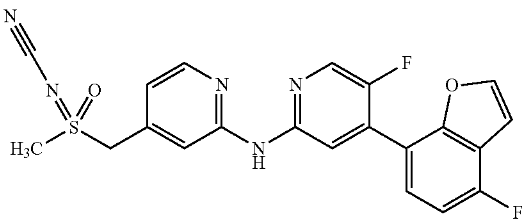 [SMILES: CS(=O)(Cc1ccnc(Nc2cc(-c3ccc(F)c4ccoc34)c(F)cn2)c1)=NC#N] | 2.6 | 146 | 56 | 1.6 |
| 10 | 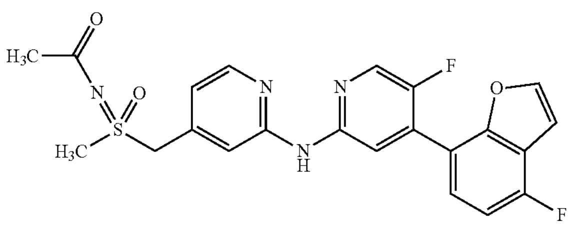 [SMILES: CC(=O)N=S(C)(=O)Cc1ccnc(Nc2cc(-c3ccc(F)c4ccoc34)c(F)cn2)c1] | 2.7 | 166 | 61 | 2.3 |
| 11 | 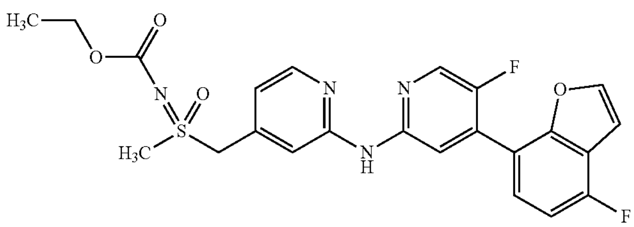 [SMILES: CCOC(=O)N=S(C)(=O)Cc1ccnc(Nc2cc(-c3ccc(F)c4ccoc34)c(F)cn2)c1] | 3.1 | 138 | 45 | 2 |
| 12 | 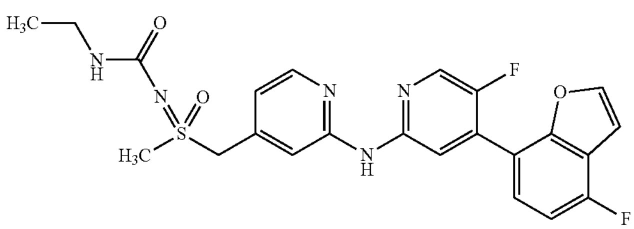 | 2.6 | 113 | 44 | 1.9 |
| 13 | 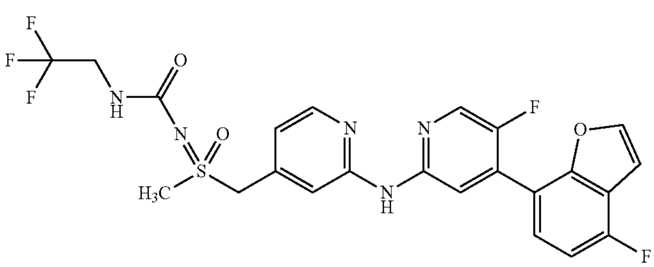 [SMILES: CS(=O)(Cc1ccnc(Nc2cc(-c3ccc(F)c4ccoc34)c(F)cn2)c1)=NC(=O)NCC(F)(F)F] | 2.6 | 280 | 108 | 2.3 |
| 14 | 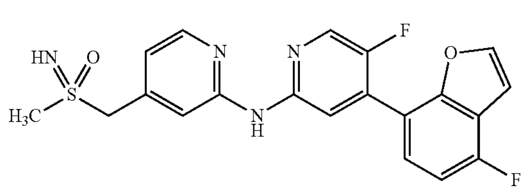 [SMILES: CS(=N)(=O)Cc1ccnc(Nc2cc(-c3ccc(F)c4ccoc34)c(F)cn2)c1] | n.t. | 142 | n.t. | n.t. |

TABLE 2-continued

| ① Example No. | Structure | ② | ③ | ④ | ⑤ |
|---|---|---|---|---|---|
| 15 | 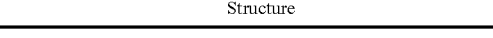 | n.t. | 121 | n.t. | n.t. |

Table 3: Inhibition of proliferation of HeLa, HeLa-MaTu-ADR, NCI-H460, DU145, Caco-2, B16F10, A2780 and MOLM-13 cells by compounds according to the present invention, determined as described under Method 3. of Materials and Methods. All $IC_{50}$ (inhibitory concentration at 50% of maximal effect) values are indicated in nM, "n.t." means that the compounds have not been tested in the respective assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation
⑨: Inhibition of MOLM-13 cell proliferation

TABLE 3

| ① | Structure | ② | ③ | ④ | ⑤ | ⑥ | ⑦ | ⑧ | ⑨ |
|---|---|---|---|---|---|---|---|---|---|
| 1 | | 30 | 30 | 36 | 33 | 34 | 41 | 11 | 16 |
| 2 | | 31 | 30 | 32 | 32 | 35 | 42 | n.t. | n.t. |
| 3 | | 6 | 11 | 21 | 15 | 19 | 19 | 10 | 6 |

TABLE 3-continued
Inhibition of proliferation
| ① | Structure | ② | ③ | ④ | ⑤ | ⑥ | ⑦ | ⑧ | ⑨ |
|---|---|---|---|---|---|---|---|---|---|
| 4 | 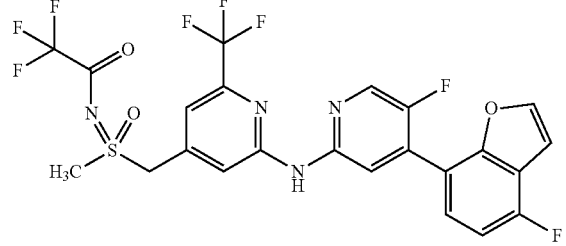 | 31 | 30 | 36 | 37 | 40 | 44 | n.t. | n.t. |
| 5 | 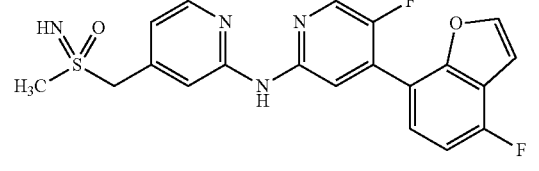 | 31 | 42 | 120 | 55 | 46 | 53 | 29 | 18 |
| 6 | 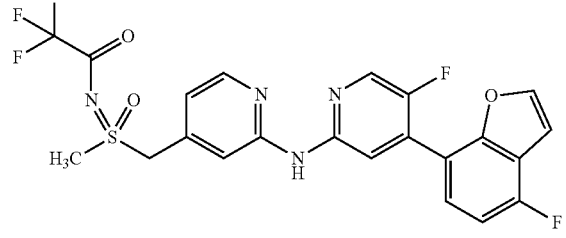 | 42 | 52 | 46 | 42 | 58 | 88 | n.t. | n.t. |
| 7 | 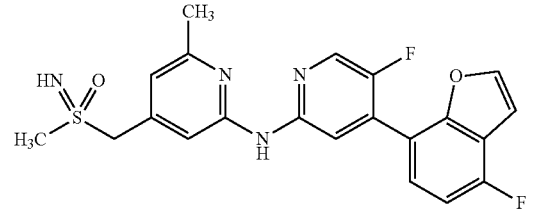 [SMILES: Cc1cc(CS(C)(=N)=O)cc(Nc2cc(-c3ccc(F)c4ccoc34)c(F)cn2)n1] | 11 | 9.1 | 33 | 14 | 14 | 17 | n.t. | 6.3 |
| 8 | 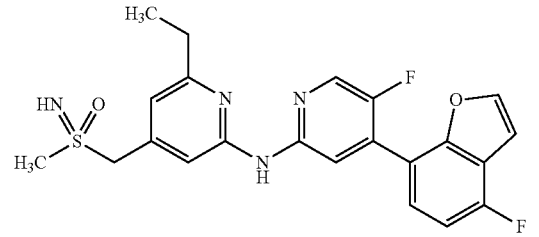 [SMILES: CCc1cc(CS(C)(=N)=O)cc(Nc2cc(-c3ccc(F)c4ccoc34)c(F)cn2)n1] | 7.6 | 8.8 | 35 | 11 | 9.4 | 32 | n.t. | 3.9 |
The invention claimed is:
1. A compound of formula (I)
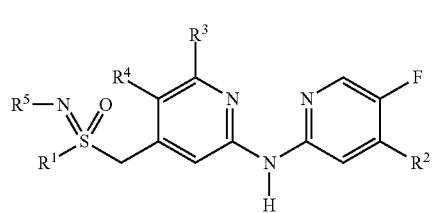
wherein:
$R^1$ is a $C_1$-$C_3$-alkyl group;
$R^2$ is the group
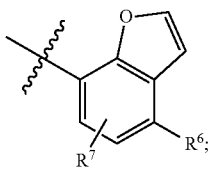
$R^3$ is a hydrogen atom a fluoro atom or a methyl-, ethyl- or trifluoromethyl-group;

R⁴ is a hydrogen atom;
R⁵ is a group selected from a hydrogen atom, cyano, —C(O)R⁹, —C(O)OR⁹, and —C(O)NR¹⁰R¹¹;
R⁶ is a group selected from a hydrogen atom, a fluoro atom and a chloro atom;
R⁷ is a hydrogen atom;
R⁹ is a methyl-, ethyl- or trifluoromethyl-group;
R¹⁰ is a C₁-C₃-alkyl group; and
R¹¹ is a hydrogen atom,
or an enantiomer, diastereomer, salt, solvate or salt of a solvate thereof.

2. The compound of formula (I) according to claim 1, wherein:
R² is the group

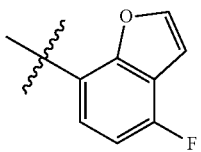 [SMILES: *c1ccc(F)c2ccoc12]

or an enantiomer, diastereomer, salt, solvate or salt of a solvate thereof.

3. The compound of formula (I) according to claim 1, wherein:
R¹ is a methyl group;
R² is the group

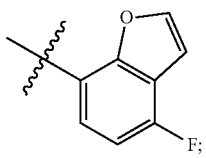 [SMILES: *c1ccc(F)c2ccoc12]

R³ is a hydrogen atom a fluoro atom, or a methyl-, ethyl- or trifluoromethyl-group;
R⁴ is a hydrogen atom;
R⁵ is a group selected from a hydrogen atom, cyano, —C(O)R⁹, —C(O)OR⁹, and —C(O)NR¹⁰R¹¹;
R⁹ is a methyl-, ethyl- or trifluoromethyl-group;
R¹⁰ is a C₁-C₃-alkyl group; and
R¹¹ is a hydrogen atom,
or an enantiomer, diastereomer, salt, solvate or salt of a solvate thereof.

4. The compound according to claim 1, which is:
(rac)-5-Fluoro-4-(4-fluoro-1-benzofuran-7-yl)-N-{6-fluoro-4-[(S-methylsulfonimidoyl)methyl]pyridin-2-yl}pyridin-2-amine;
(rac)-2,2,2-Trifluoro-N-{[(2-fluoro-6-{[5-fluoro-4-(4-fluoro-1-benzofuran-7-yl)pyridin-2-yl]amino}pyridin-4-yl)methyl](methyl)oxido-λ⁶-sulfanylidene}acetamide;
(rac)-5-Fluoro-4-(4-fluoro-1-benzofuran-7-yl)-N-{4-[(S-methylsulfonimidoyl)methyl]-6-(trifluoromethyl)pyridin-2-yl}pyridin-2-amine;
(rac)-2,2,2-Trifluoro-N-[{[2-{[5-fluoro-4-(4-fluoro-1-benzofuran-7-yl)pyridin-2-yl]amino}-6-(trifluoromethyl)pyridin-4-yl]methyl}(methyl)oxido-λ⁶-sulfanylidene]acetamide;
(rac)-5-Fluoro-4-(4-fluoro-1-benzofuran-7-yl)-N-{4-[(S-methylsulfonimidoyl)methyl]pyridin-2-yl}pyridin-2-amine;
(rac)-2,2,2-Trifluoro-N-{[(2-{[5-fluoro-4-(4-fluoro-1-benzofuran-7-yl)pyridin-2-yl]amino}pyridin-4-yl)methyl](methyl)oxido-λ⁶-sulfanylidene}acetamide;
(rac)-5-Fluoro-4-(4-fluoro-1-benzofuran-7-yl)-N-{6-methyl-4-[(S-methylsulfonimidoyl)methyl]pyridin-2-yl}pyridin-2-amine;
(rac)-N-{6-Ethyl-4-[(S-methylsulfonimidoyl)-methyl]pyridin-2-yl}-5-fluoro-4-(4-fluoro-1-benzofuran-7-yl)pyridin-2-amine;
(rac)-{[(2-{[5-fluoro-4-(4-fluoro-1-benzofuran-7-yl)pyridin-2-yl]amino}pyridin-4-yl)methyl](methyl)oxido-λ⁶-sulfanylidene}cyanamide;
(rac)-N-{[(2-{[5-fluoro-4-(4-fluoro-1-benzofuran-7-yl)pyridin-2-yl]amino}pyridin-4-yl)methyl](methyl)oxido-λ⁶-sulfanylidene}acetamide;
(rac)-Ethyl {[(2-{[5-fluoro-4-(4-fluoro-1-benzofuran-7-yl)pyridin-2-yl]amino}pyridin-4-yl)methyl](methyl)oxido-λ⁶-sulfanylidene}carbamate;
(rac)-1-Ethyl-3-{[(2-{[5-fluoro-4-(4-fluoro-1-benzofuran-7-yl)pyridin-2-yl]amino}pyridin-4-yl)methyl](methyl)oxido-λ⁶-sulfanylidene}urea;
(rac)-1-{[(2-{[5-Fluoro-4-(4-fluoro-1-benzofuran-7-yl)pyridin-2-yl]amino}pyridin-4-yl)methyl](methyl)oxido-λ⁶-sulfanylidene}-3-(2,2,2-trifluoroethyl)urea;
(+)-5-Fluoro-4-(4-fluoro-1-benzofuran-7-yl)-N-{4-[(S-methylsulfonimidoyl)methyl]pyridin-2-yl}pyridin-2-amine; or
(−)-5-Fluoro-4-(4-fluoro-1-benzofuran-7-yl)-N-{4-[(S-methylsulfonimidoyl)methyl]pyridin-2-yl}pyridin-2-amine,
or an enantiomer, diastereomer, salt, solvate or salt of a solvate thereof.

5. The compound of claim 1 or a salt thereof.
6. The compound of claim 4 or a salt thereof.
7. A pharmaceutical composition comprising the compound according to claim 1, or an enantiomer, diastereomer, salt, solvate or salt of a solvate thereof, in combination with a pharmaceutically suitable adjuvant.
8. The pharmaceutical composition of claim 7 comprising the compound of formula (I) or a salt thereof.
9. A method for treatment of melanomas, cervical carcinomas, lung carcinomas, ovarian carcinomas, prostate carcinomas, colorectal carcinomas or leukemias comprising administering to a subject in need thereof a therapeutically effective amount of the compound according to claim 1, or an enantiomer, diastereomer, salt, solvate or salt of a solvate thereof.
10. The method of claim 9, comprising administering to the subject in need thereof a therapeutically effective amount of the compound of formula (I) or a salt thereof.
11. A method for treatment of melanomas, non-small cell lung carcinomas, ovarian carcinomas, hormone-independent human prostate carcinomas, multidrug-resistant human cervical carcinomas, colorectal carcinomas or acute myeloid leukemias comprising administering to a subject in need thereof a therapeutically effective amount of the compound according to claim 1, or an enantiomer, diastereomer, salt, solvate or salt of a solvate thereof.
12. The method of claim 11, comprising administering to the subject in need thereof a therapeutically effective amount of the compound of formula (I) or a salt thereof.

* * * * *